(12) United States Patent
Sedic

(10) Patent No.: US 11,344,470 B2
(45) Date of Patent: May 31, 2022

(54) PERSONAL MASSAGE APPARATUSES FOR MEN AND METHODS OF USE

(71) Applicant: Filip Sedic, Shanghai (CN)

(72) Inventor: Filip Sedic, Shanghai (CN)

(73) Assignee: LELO Inc., San Jose, CA (US)

( * ) Notice: Subject to any disclaimer, the term of this patent is extended or adjusted under 35 U.S.C. 154(b) by 322 days.

(21) Appl. No.: 16/520,675

(22) Filed: Jul. 24, 2019

(65) Prior Publication Data

US 2020/0046599 A1 Feb. 13, 2020

Related U.S. Application Data

(60) Provisional application No. 62/716,458, filed on Aug. 9, 2018.

(51) Int. Cl.
*A61H 19/00* (2006.01)
*A61F 5/41* (2006.01)

(52) U.S. Cl.
CPC ............ *A61H 19/32* (2013.01); *A61F 5/41* (2013.01); *A61F 2005/411* (2013.01); *A61H 2201/0107* (2013.01); *A61H 2201/0192* (2013.01); *A61H 2201/1207* (2013.01); *A61H 2201/1692* (2013.01); *A61H 2201/5079* (2013.01)

(58) Field of Classification Search
CPC ........ A61H 19/00; A61H 19/32; A61H 23/02; A61H 19/44; A61H 23/0218; A61H 2201/5058; A61H 2201/5079; A61H 19/23; A61H 21/00; A61H 2023/0272; A61H 23/0263; A61H 23/00; A61F 5/41; A61F 2005/417
See application file for complete search history.

(56) References Cited

U.S. PATENT DOCUMENTS

| | | | |
|---|---|---|---|
| 9,138,372 B2 | 9/2015 | Dorronsoro Rueda | |
| 10,310,805 B2 * | 6/2019 | Barasch | A61H 19/00 |
| 10,940,077 B2 * | 3/2021 | Driscoll | A61H 19/00 |
| 2003/0171647 A1 | 9/2003 | Garland | |
| 2004/0204626 A1 * | 10/2004 | Humphries, Jr. | A61F 5/00 |
| 2006/0264856 A1 | 11/2006 | Wong | |
| 2009/0099413 A1 * | 4/2009 | Kobashikawa et al. | A61F 5/00 |
| 2014/0378759 A1 * | 9/2014 | Fang et al. | A61H 19/00 |
| 2016/0008218 A1 * | 1/2016 | Murison | A61H 23/00 |

(Continued)

FOREIGN PATENT DOCUMENTS

| | | | | |
|---|---|---|---|---|
| WO | WO9503762 A1 * | 7/1994 | | A61F 5/41 |
| WO | WO2007096595 A2 * | 2/2007 | | A61H 19/00 |

(Continued)

OTHER PUBLICATIONS

Satisfyer US, "Satisfyer Men," www.satisfyer.com, pp. 1-9, accessed Jul. 31, 2018.

*Primary Examiner* — Samchuan C Yao
*Assistant Examiner* — Tyler A Raubenstraw
(74) *Attorney, Agent, or Firm* — Evan Feldstein

(57) ABSTRACT

An example personal massage apparatus for men includes a main body having a sheath, a shell disposed adjacent the main body, a first motor, a second motor, a first sensor, a second sensor, a third sensor, a battery, and a controller. The personal massage apparatus is configured to collect data based on a user's use of the apparatus and transmit said data to a second device, such as a mobile phone, for collection and analysis.

16 Claims, 25 Drawing Sheets

(56) References Cited

U.S. PATENT DOCUMENTS

| | | | |
|---|---|---|---|
| 2016/0015595 A1* | 1/2016 | Blenk et al. | A61H 23/02 |
| 2016/0235580 A1* | 2/2016 | Trost | A61F 5/41 |
| 2018/0049942 A1* | 2/2018 | Chan et al. | A61H 19/32 |
| 2018/0116904 A1* | 5/2018 | Lieberman et al. | A61H 19/34 |
| 2019/0015291 A1* | 1/2019 | Sedic | A61H 19/34 |
| 2019/0209426 A1* | 3/2019 | Swartz | A61H 19/34 |
| 2020/0188221 A1* | 6/2020 | Lenke | A61H 19/34 |

FOREIGN PATENT DOCUMENTS

| | | | | |
|---|---|---|---|---|
| WO | WO2013006264 A2 * | 6/2012 | | A61H 1/00 |
| WO | WO2015060717 A1 * | 4/2015 | | A61H 11/00 |
| WO | WO-2018058234 A1 * | 4/2018 | | A61H 19/34 |

\* cited by examiner

PERSONAL MASSAGE APPARATUSES FOR MEN AND METHODS OF USE

CROSS-REFERENCE TO RELATED APPLICATIONS

This application claims the benefit U.S. Provisional Patent Application No. 62/716,458, filed Aug. 9, 2018, which is incorporated into this disclosure in its entirety.

FIELD

The disclosure relates generally to the field of personal massage apparatuses and methods of use. More particularly, the disclosure relates to personal massage apparatuses designed to be used by men on erogenous zones of their bodies.

BACKGROUND

Personal massage apparatuses designed to be used by men may include several devices configured to provide stimuli to a portion of a human body. Examples of such devices include vibrators, insertion devices, and devices configured to simulate the look and feel of a penis, scrotum, or anus. These devices focus on the pleasure of a male user.

While such devices may indeed provide pleasure to a male user, some men seek to improve upon their sexual performance while still obtaining pleasure. More specifically, male users often wish to improve upon their sexual technique, stamina, and overall performance generally, while also receiving pleasurable stimulation. Additionally, users may wish to receive data based on performance and/or their own physical statistics in order to track improvement over time. The art does not include such devices.

Accordingly, a need for personal massage apparatuses that can stimulate the body of a user, teach a user how to improve his sexual performance, and track data related to a user's performance is needed.

BRIEF SUMMARY OF EXAMPLES

Various example personal massage apparatuses and methods of use are described and illustrated herein.

An example personal massage apparatus configured to stimulate a penis of a user comprises an elongate, tubular main body having an open first end, a closed second end, a middle portion extending from the first end to the second end, and an elongate, flexible sheath disposed within the main body having a proximal end and a distal end, the sheath defining a chamber extending from an opening defined by the proximal end of the sheath to the distal end of the sheath, the sheath being attached to the first end of the main body and comprised of silicone, the sheath configured to receive said penis of said user within the chamber, an elongate, tubular shell attached to and surrounding substantially all of the middle portion of the main body, the shell being comprised of metal a motor disposed within the main body and adjacent the sheath, the motor configured to produce vibrations in order to stimulate said penis, a controller disposed within the main body and configured to operate the motor, and a first sensor disposed within the main body and adjacent an exterior surface of the sheath, the sensor configured to sense the proximity of said user to the first sensor.

Another example personal massage apparatus configured to stimulate a penis of a user comprises an elongate, tubular main body having an open first end, a closed second end, a middle portion extending from the first end to the second end, and an elongate, flexible sheath disposed within the main body having a proximal end and a distal end, the sheath defining a chamber extending from an opening defined by the proximal end of the sheath to the distal end of the sheath, the sheath being attached, to the first end of the main body and comprised of silicone, the sheath configured to receive said penis of said user within the chamber, an elongate, tubular shell attached to and surrounding substantially all of the middle portion of the main body, the shell being comprised of metal, a motor disposed within the main body and adjacent the sheath, the motor configured to produce vibrations in order to stimulate said penis, a controller disposed within the main body and configured to operate the motor, a first sensor disposed within the main body and adjacent an exterior surface of the sheath, the sensor configured to sense the proximity of said user to the first sensor, the first sensor comprising a capacitive sensor, and a second sensor disposed within the main body and adjacent the motor, the second sensor configured, to detect output produced by the motor.

Another example personal massage apparatus configured to stimulate a penis of a user comprises m elongate, tubular main body having an open first end, a closed second end, a middle portion extending from the first end to the second end, and an elongate, flexible sheath disposed within the main body having a proximal end and a distal end, the sheath defining a chamber extending from an opening defined by the proximal end of the sheath to the distal end of the sheath, the sheath being attached to the first end of the main body and comprised of silicone, the sheath, configured to receive said penis of said user within the chamber, an elongate, tubular shell attached to and surrounding substantially all of the middle portion of the main body, the shell being comprised of metal, a motor disposed within the main body and adjacent the sheath, the motor configured to produce vibrations in order to stimulate said penis, a controller disposed within the main body and configured to operate the motor, a first sensor disposed within the main body and adjacent an exterior surface of the sheath, the sensor configured to sense the proximity of said user to the first sensor, the first sensor comprising a capacitive sensor, a second sensor disposed within the main body and adjacent the motor, the second sensor configured to detect output produced by the motor, and a third sensor disposed on the controller, the third sensor configured to detect the orientation of the main body.

Additional understanding of the claimed apparatuses and methods can be obtained by reviewing the detailed description of selected examples, below, with reference to the appended drawings.

DESCRIPTION OF EMBODIMENTS

Figure 1:
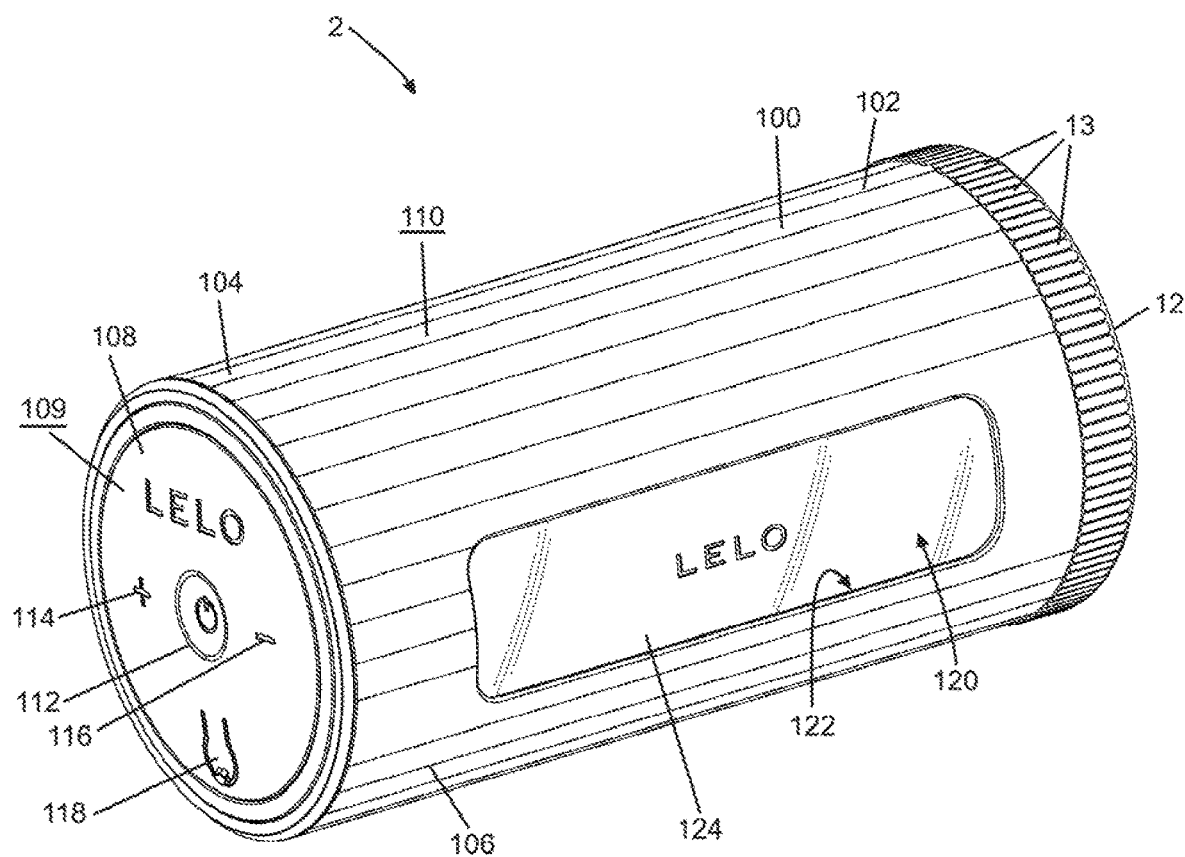
FIG. 1 is a perspective view of an example personal massage apparatus.
Figure 2:
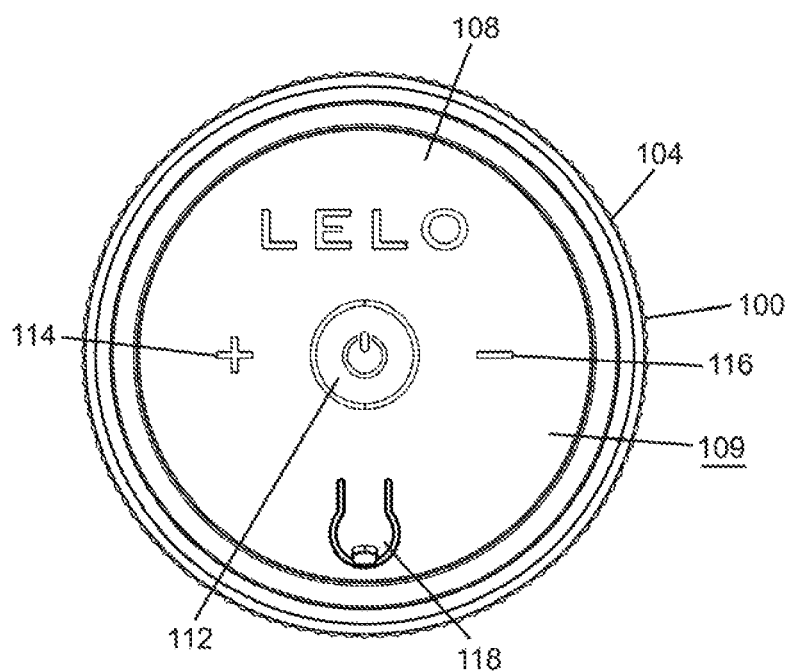
FIG. 2 is a bottom view of the personal massage apparatus illustrated in FIG. 1.

The following detailed description and the appended drawings describe and illustrate various example devices suitable for use as personal massage apparatuses. The description and drawings are provided to enable one skilled in the art to make and use one or more example personal massage apparatuses. They are not intended to limit the scope of the claims in any manner.

FIGS. 1, 2, 3, 4, 5, 6, 7, 8, 9, 10, and 11 illustrate an example personal massage apparatus 2 configured to be used by men and/or one or more components thereof. The personal massage apparatus 2 comprises a main body 10, a shell 100, and first motor 200, a second motor 250, a first sensor 300, a second sensor 330, a third sensor (not illustrated in the FIGS.), a controller 400, a battery 450, and various other components that will be described in greater detail below.

The main body 10 is elongate and tubular and includes a first end 12, a second end 14, and a middle portion 16 extending from the first end 12 to the second end 14, in the illustrated embodiment, the first end 12 is open and the second end 14 is closed. Each of the first and second ends 12, 14 are substantially circular in shape and the first end 12 defines an opening 18, which is also substantially circular in shape. The first end 12 and the opening 18 are configured to cooperatively allow a user to insert a portion of himself into a chamber 46 defined by the main body 10. The main body 10 is substantially cylindrical in shape along the middle portion 16 and it houses various components described below. The opening 18 defines a first diameter $d_1$, as well. The second end 14 and middle portion 16 of the main body 10 are comprised of plastic in the illustrated embodiment, while the first end 12 is comprised of silicone. The first end 12 includes a set of ridges 13, as well. A skilled artisan will be able to select suitable components of the main body according to a particular example based on various considerations, including the size and shape of the penis of the potential user, the desired length of the main body, and the desired weight of the main body. In other embodiments, the first end, second end, and middle portion of the main body may be comprised of any suitable material. In various embodiments, the main body may have any shape, including that of a cone, pyramid, box, and any other suitable shape into which a user may insert his penis. In different embodiments, the opening of the first end may have any shape, including feat of a triangle, ellipse, oval, square, rectangle, and pentagon. In other embodiments, the first diameter may be between about 4 centimeters ("cm") and about 16 cm, between about 6 cm and about 14 cm, and between about B cm and about 12 cm. In additional embodiments, the length of the main, body from the first to the second end may be between about 8 cm and about 30 cm, between about 12 cm and about 26 cm, and between about 16 cm and about 22 cm. In other embodiments, the first end may not define ridges.

The main body 10 also includes an elongate, flexible sheath 30 disposed within the main body 10 having a proximal end 32, a distal end 34, a middle portion 35 extending front the proximal end 32 to the distal end 34, an inner surface 36, and an outer surface 38. The proximal end 32 is attached to the first end 12 and defines an opening 40 has a diameter that is only slightly smaller than that of the first end 12. The opening 40 is substantially circular in shape and provides a way of entry into the chamber 46 that is cooperatively defined by the proximal end 32, distal end 34, and middle portion 35, and extends from the proximal end 32 to the distal end 34. The proximal cud 32 is configured to allow a user to insert his penis into the sheath 30 via the opening 40 such that the head of a user's penis will be placed adjacent the distal end 34, the base of the penis will be adjacent the proximal end 32, and the shaft of the penis will extend along the middle portion 35. The sheath 30 decreases in diameter along its length until it reaches approximately halfway between the proximal end 32 and the distal end 34. At that point, the sheath 30 increases in diameter as it extends toward the distal end 34 until it reaches the second diameter $d_2$, which is the maximum diameter of the distal end 34 of the sheath 30. The distal end 34 of the sheath 30 then decreases in diameter from the portion of the sheath 30 having a maximum diameter to the tip 42 of the sheath. This structure is configured to contour to the sizes and shapes of the typical human penis and provide maximum contact and pleasure to the penis once it has been inserted into the sheath 30.

Figure 3:
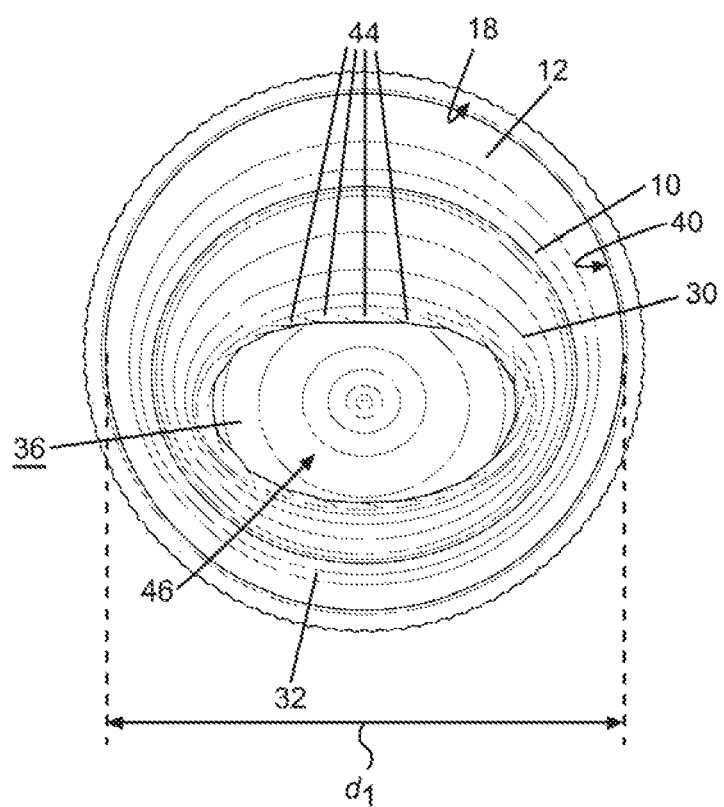
FIG. 3 is a top view of the personal massage apparatus illustrated in FIG. 1.
Figure 4:
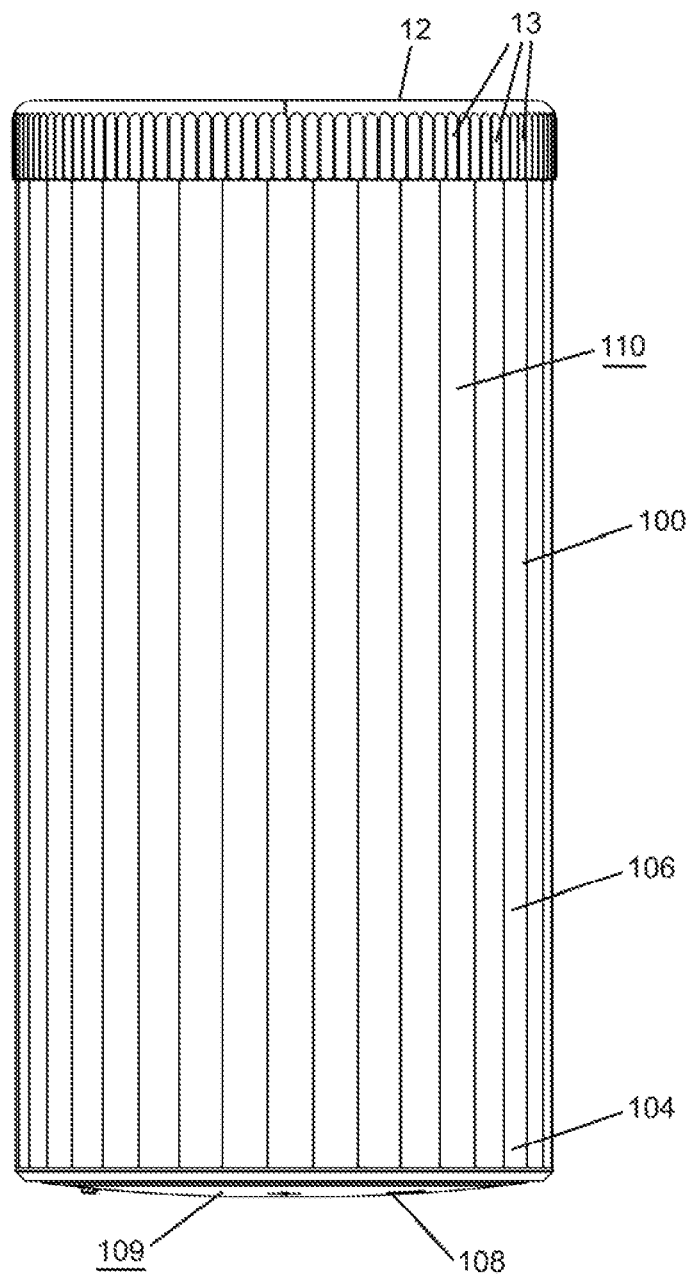
FIG. 4 is an end view of the personal massage apparatus illustrated in FIG. 1.
Figure 5:
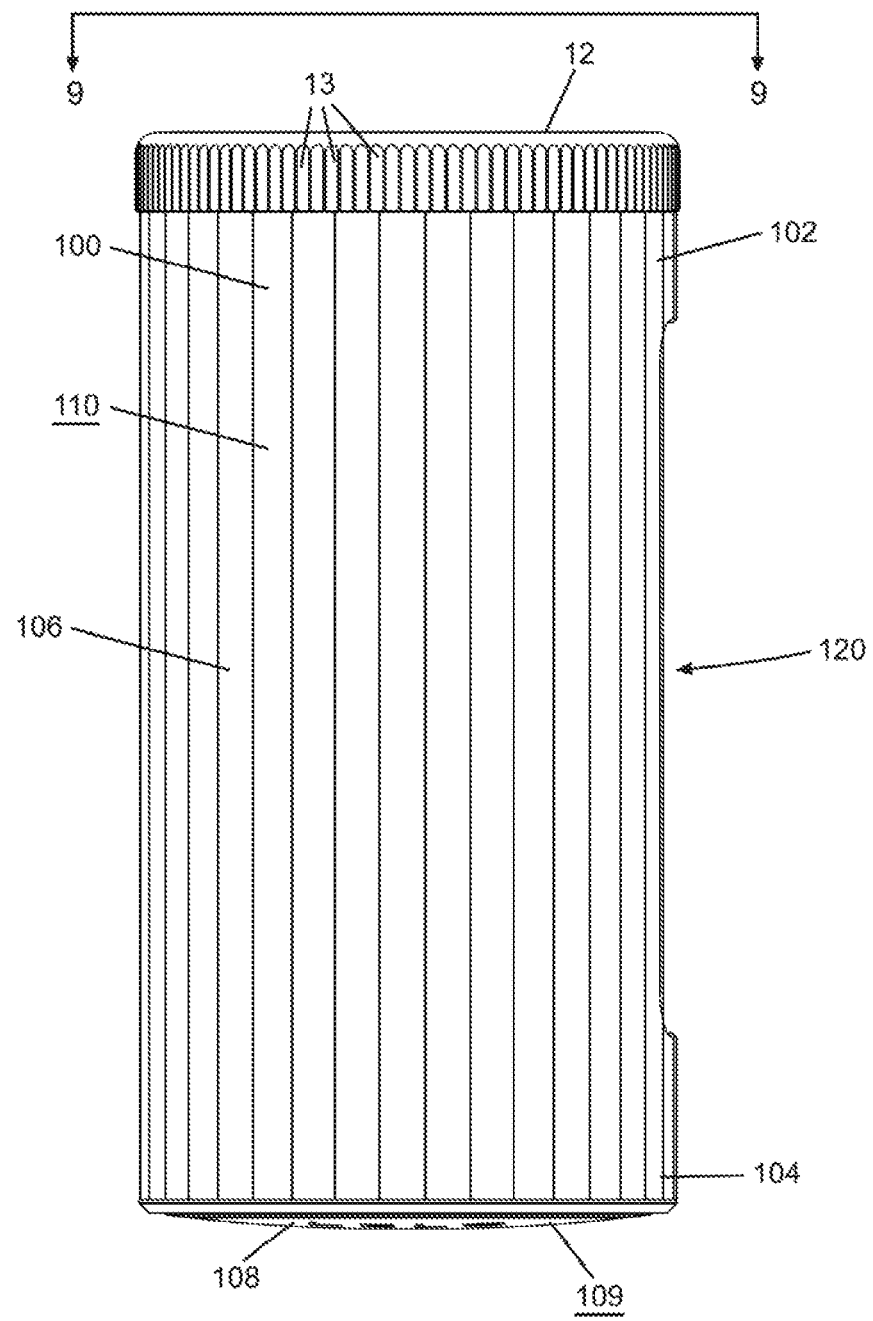
FIG. 5 is a side view of the personal massage apparatus illustrated in FIG. 1.
Figure 6:
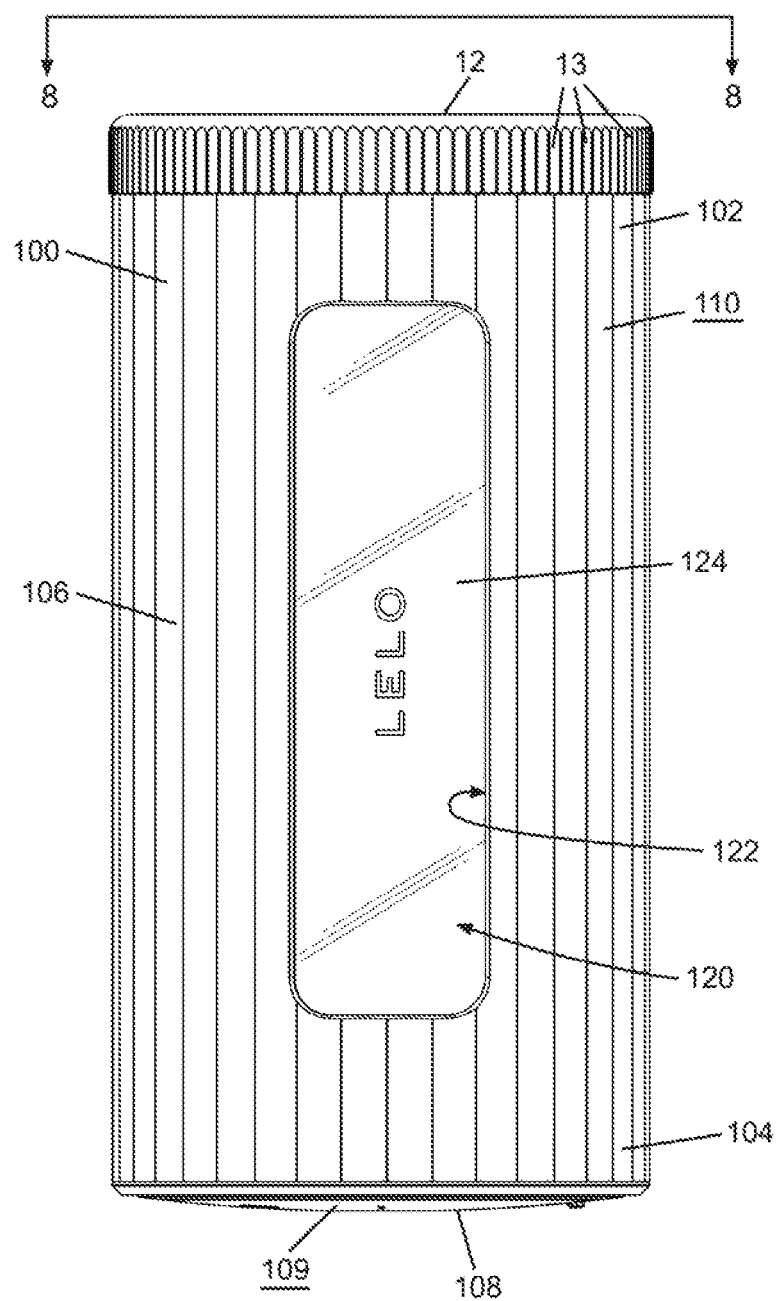
FIG. 6 is another end view of the personal massage apparatus illustrated in FIG. 1.
Figure 7:
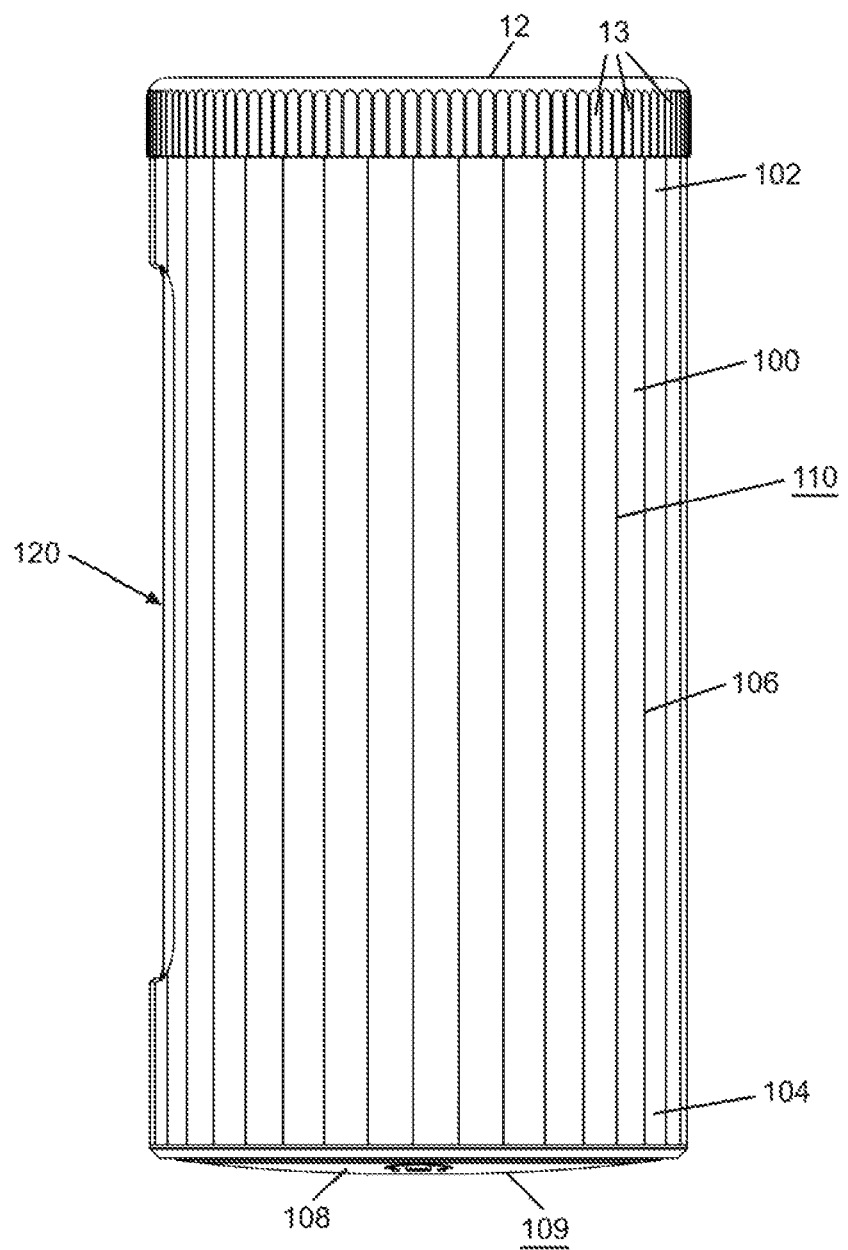
FIG. 7 is another side view of the personal massage apparatus illustrated in FIG. 1.

In the illustrated embodiment, the sheath 30 is comprised of silicone. The silicone is high-quality, medical-grade silicone that repels bacteria. It is sufficiently soft to provide pleasure to a user, while also being durable enough to endure repeated use. The inner surface 36 of the sheath 30 optionally, as is illustrated, defines grooves 44 extending along the middle portion 35. The grooves 44 are configured to increase stimulation to the user and are best illustrated in FIG. 3.

Additionally, the main body 10 includes a first support column 48 and a second support column 49 disposed within the cavity 20 of the main body 10. The first and second support columns 48, 49 extend from the middle portion 16 of the main body 10 to the outer surface 38 of the middle portion 35 of the sheath 30. The support columns 48, 49 are configured to maintain the sheath 30 generally in position within the main body 10 and are comprised of plastic surrounded by a layer of silicone.

A skilled artisan will be able to suitably configure the sheath according to a particular example based on various considerations, including the size and shape of the penis of the user, the desired length of the sheath, and the desired feel of the inner surface of the sheath. In other embodiments, the sheath may be comprised of any suitable materials, such as one or more elastic and/or elastomeric materials, rather than silicone; any suitable material may be used. In various embodiments, the sheath may have any shape, including that of a cone, pyramid, box, and any other suitable shape into which a user may insert his penis. In alternative embodiments, the sheath may be uniform in diameter along its length, may decrease in diameter from the proximal end to the distal end, may increase in diameter from the proximal end to the distal end, and may fluctuate in diameter along the middle portion. In different embodiments, the opening of the proximal end may have any shape, including that of a triangle, ellipse, oval, square, rectangle, and pentagon. In other embodiments, the second diameter may be between about 4 centimeters ("cm") and about 16 cm, between about 6 cm and about 14 cm, and between about 8 cm and about 12 cm. In additional embodiments, the length of the sheath from the proximal end to the distal end may be between about 8 cm and about 20 cm, between about 10 cm and about 18 cm, and between about 12 cm and about 16 cm. In alternative embodiments, the first and second support columns may be omitted, there may be one, three, or more than three support columns, and the support columns may be comprised of any suitable material.

The personal massage apparatus also includes a shell 100 attached to and surrounding a significant portion of the main body 10. The shell 100 includes a first end 102, a second end 104, a middle portion 106 extending from the first end 102 to the second end 104, and an endpiece 108 defining a portion of the second end 104. The shell 100 is substantially cylindrical in shape and, like the main body 10, has an open first end 102 and a closed second end 104. The shell 100 is disposed about and surrounds a significant portion of the main body 10. The first end 102 of the shell 100 is substantially adjacent the first end 12 of the main body 10, while the second end 104 and endpiece 108 of the shell 100 are substantially adjacent the second end 14 of the main body 10. Accordingly, the middle portion 106 of the shell 100 is adjacent the middle portion 16 of the main body 10. The first end 102 defines m opening (not illustrated in the FIGS.) that allows the main body 10 to be placed within the shell 100 during assembly. In the illustrated embodiment, however, the main body 10 is not immoveable from the shell 100 once assembled. The opening of the shell 100 also defines a diameter which is slightly larger than that of the middle portion 16 of the main body 10. The shell 100 is configured to fit snugly about the main body 10. The shell 100 and main body 10 may be secured to one another via any suitable mechanism. A skilled artisan will be able to suitably configure the shell according to a particular example based on various considerations, including the size and shape of the main body, the desired length and thickness of the shell, and the desired weight of the personal massage apparatus. In various embodiments, the shell may have any shape, including that of a cone, pyramid, box, and another suitable, shape, so long as it surrounds the main body. In different embodiments, the shell may only surround a portion of the main body, may comprise a portion of the same, and/or may extend past the first end of the main body. In additional embodiments, the length of the shell from the first end to the second end may be between about 10 cm and about 34 cm, between about 16 cm and about 30 cm, and between about 20 cm and about 26 cm. In yet other embodiments, the shell may be attached to the main body via an adhesive or via any physical mechanism(s), such as hooks or similar items designed to hold pieces of an apparatus together.

In the illustrated embodiment, the shell 100 is primarily comprised of aluminum; indeed, the majority of the middle portion 100 and exterior surface 110 thereof are comprised of aluminum. However, the endpiece 108 is comprised of silicone, which contacts a portion of the middle port ion 106 that is adjacent the distal end 104. In other embodiments, however, any portion of the shell, may be comprised of silicone, aluminum, or any other suitable material. A skilled artisan will be able to select a suitable material for the shell, including the endpiece, according to a particular example based on various considerations, including whether the endpiece has a use other than a structural use and the shape and size of the main body. In various embodiments, all or a portion of the shell may be comprised of various materials including plastic and/or one or more metals, and the endpiece may be comprised of any suitable material, including an elastic, metal, or plastic.

Figure 9:
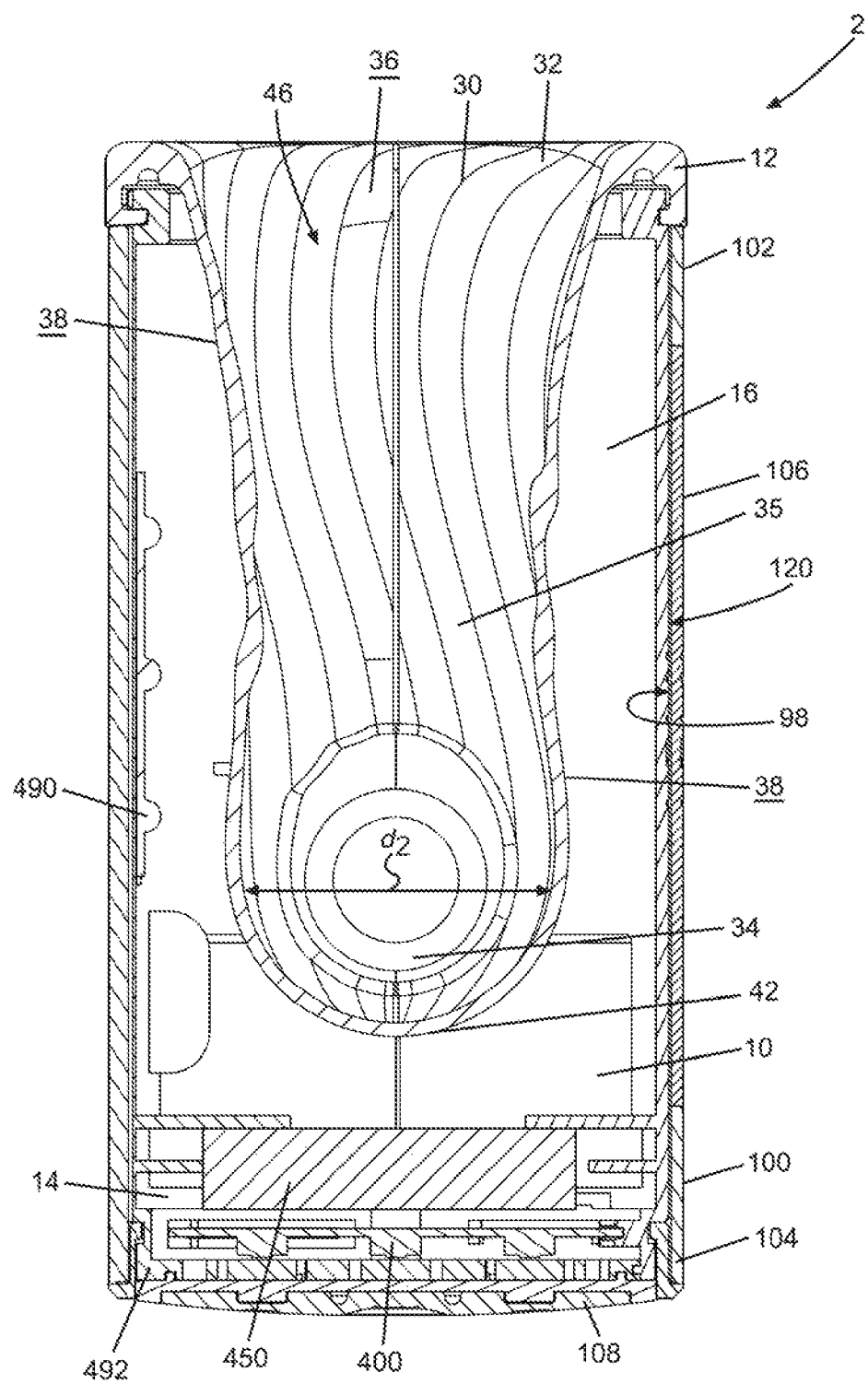
FIG. 9 is a cross-sectional view of the personal massage apparatus illustrated in FIG. 5, taken along line 9-9.
Figure 10:
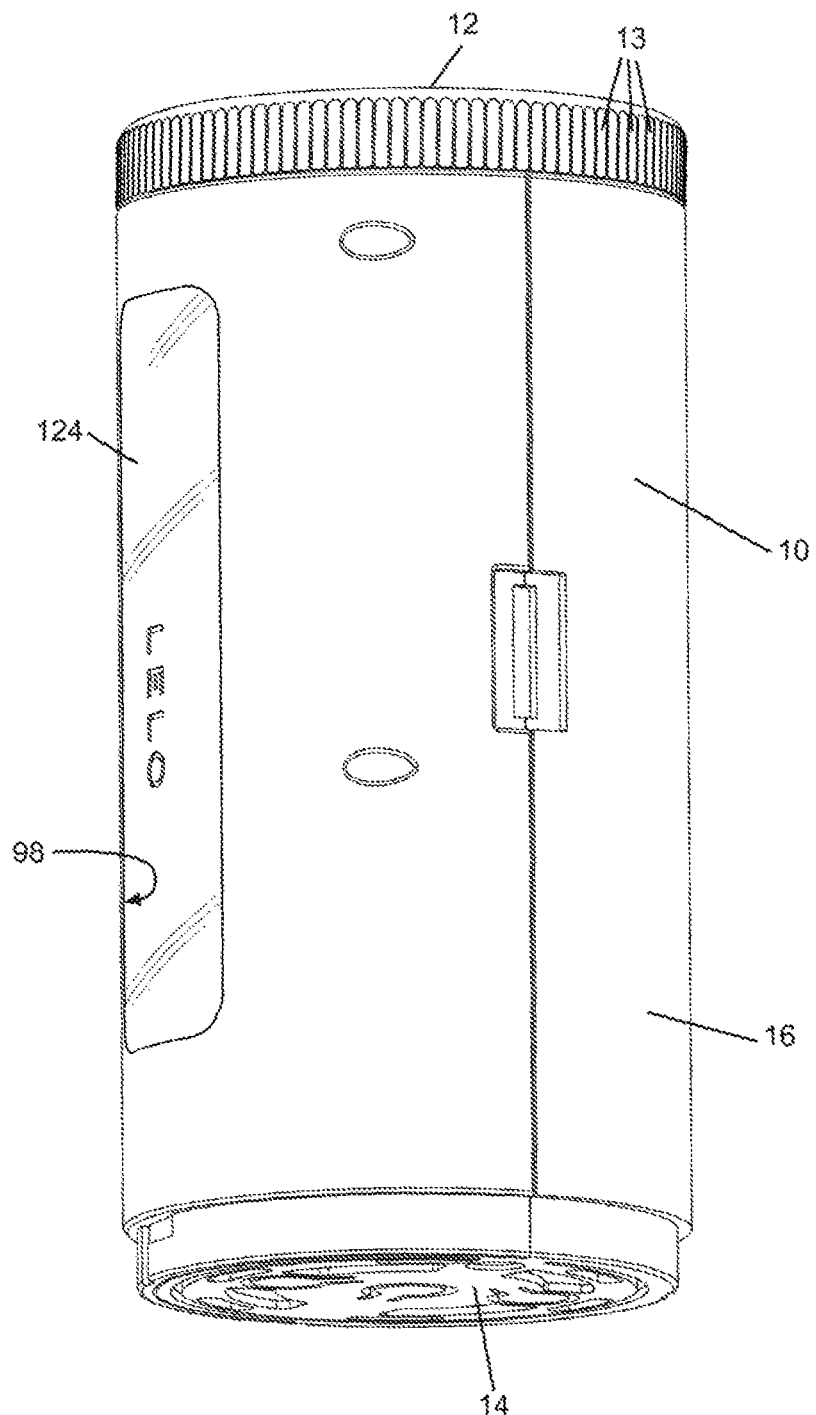
FIG. 10 is a perspective view of the main body of the personal massage apparatus illustrated in FIG. 1 separate from the shell.
Figure 11:
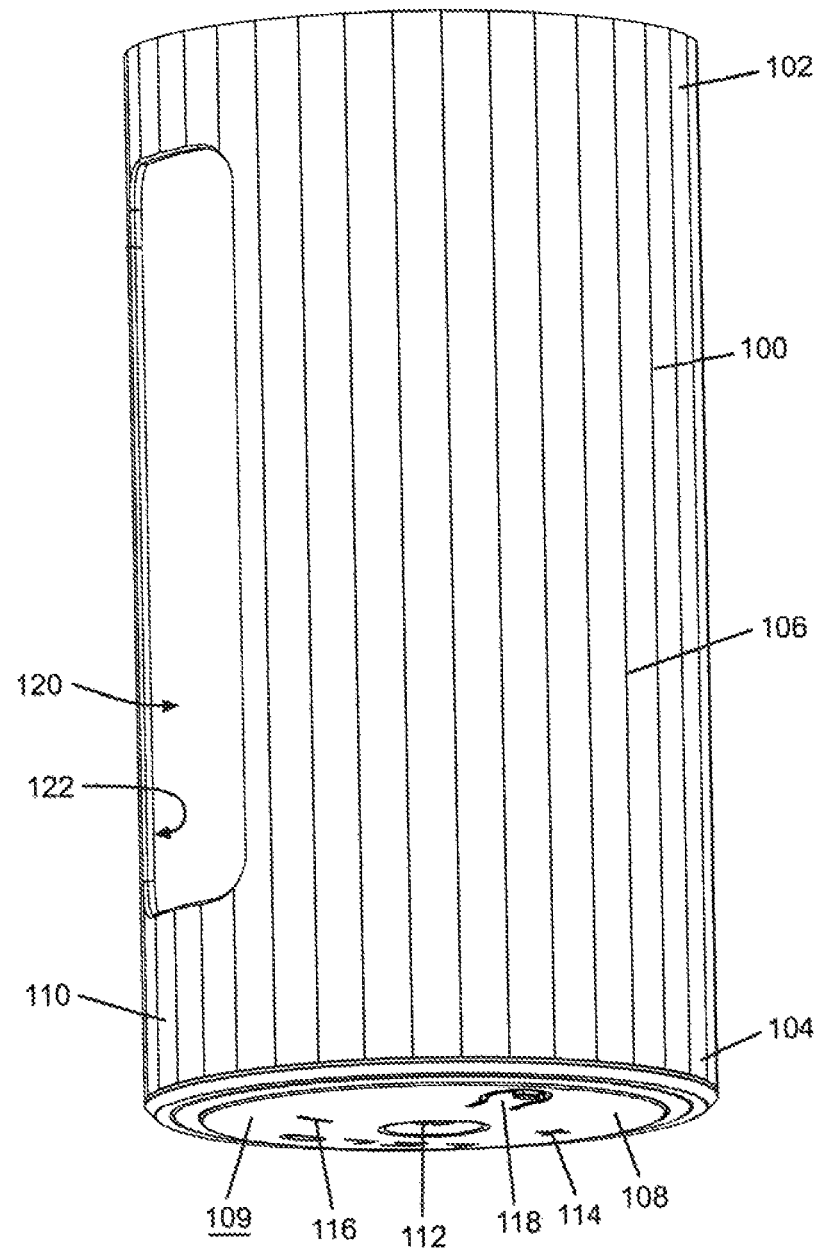
FIG. 11 is a perspective view of the shell of the personal massage apparatus illustrated in FIG. 1 separate from the main body.

Optionally, and as is shown in the Illustrated embodiment, the main body 10 and shell 100 may cooperatively define a viewing panel 120. As best illustrated in FIGS. 1 and 9, the shell 100 defines a first window 122 extending along its middle portion 106 and the main body 10 defines a second window 98 extending along its middle portion 16. The first and second windows 122, 98 are adjacent and line up with one another so that a user may see various components (such as, for example, various sensor and motors, described below) that are disposed within the main body 10. The viewing panel 120, therefore, is cooperatively defined by the first and second windows 122, 98. In such an embodiment, the personal massage apparatus 2 includes a plastic cover 124 that is configured to snugly fit into the portion of personal massage apparatus 2 that defines the viewing panel 120. The cover 124 forms a protective seal with the personal massage apparatus 2 and helps to prevent outside debris or other material from entering the interior of the device. The viewing panel 120 is rounded rectangular in shape and the cover 124 is not removable in the illustrated embodiment. A skilled artisan will be able to select suitable components for and suitably form the viewing panel according to a particular example based on various considerations, including whether a viewing panel is desired and the desired shape and size of the same. In other embodiments, the personal massage apparatus may define zero, two, three, four, or more than four viewing panels. In different embodiments, the viewing panel may have any shape, including shapes which are circular, rectangular, triangular, pentagonal, and elliptical. In alternative embodiments, the cover may be comprised of any suitable material and it may or may not be immoveable. In various embodiments, the window may be defined by any portion of the personal massage apparatus.

The endpiece 108 forms a portion of the second end 104 of the shell 100 and is disposed substantially adjacent the second end 14 of the main body 10. The endpiece 108 includes user controls on its lower surface 109 that comprise first, second, and third 112, 114, 116 user controls that communicate with the controller 400 to operate the personal massage apparatus 2. The first user control 112 allows a user to power on the device and select a particular setting for the device (i.e., high frequency, low frequency, a particular pattern etc.). It also allows a user to power off the device. The second user control 114 allows a user to increase the speed and/or intensity of the vibrations produced by the first and/or second motors 200, 250. The third user control 116 allows a user to decrease the speed and/or intensity of the vibrations produced by the first and/or second motors 200, 250. The endpiece 108 also includes a charging port 118 that provides a user access to the battery 450, as described in greater detail below. Optionally, the charging port 118 may include a cover 118a, as illustrated, to prevent dust and debris from entering the charging port 118 itself. The cover 118a is formed from a portion of the endpiece 108. In various embodiments, zero, one, two, four, or more than four user controls may be included, and they may control any aspect of operation of the device. The charging port may be covered by a flap or other covering various embodiments, as well.

As described previously, the main body 10 houses various internal components. One such component is the controller 400. The controller 400 is disposed adjacent the second end 14 of the main body 10. It is most clearly visible in FIGS. 8 and 9. The controller 400 can activate at least the first and second motors 200, 250 and first 300, second 330, and third sensors in response to receiving a control signal and is supplied with power by the battery 450, each of which is described in greater detail below. The controller 400, for example, can change the production of stimulating waves and/or vibrations generated by the first and second motors 200, 250 by altering the rate, strength, and/or duration of the output of the same. The controller 400 comprises a printed circuit board assembly in the illustrated embodiment; however, it may be comprised of any suitable device and/or material in other embodiments. Suitable examples include a printed circuit board and an electrical circuit board. The controller 400 includes a memory that has the capability to store-multiple pre-set stimulation patterns. For example, the controller 400 may store stimulation patterns at various intensities (e.g., low, medium, high), stimulation pattern, that may comprise various bursts of stimulation, and/or stimulation patterns including periods of stimulation followed by stimulation-free periods. Moreover, the controller 400, allows a user to choose stimulation patterns and their intensities through the first, second, and third 112, 114, 116 user controls, as described above. Optionally, the controller 400 may also be programmed by the user to store stimulation patterns that are particularly suitable to the user or of a user's creation. Additionally, in other embodiments, the controller may be controlled by an external source (not illustrated in the Figures), such as a remote control or a wireless signal emitted through one or more of a mobile phone, tablet, computer, or other similar devices. The external source may provide the controller stimulation patterns that are not stored on the memory of the controller.

In this embodiment, the controller 400 is operatively connected to an interface 410, which allows it to communicate with a second device, such as a personal computer, tablet, mobile telephone, or other electronic device (not illustrated in the Figures). Using the interface 410, the personal massage apparatus 2 can send information to other devices so that the other device(s) may collect data pertaining to the use of the personal massage apparatus 2. Additionally, in some embodiments, the personal massage apparatus may receive control signals from another device that can indicate that the personal massage apparatus should turn on or off, increase or decrease speed, switch to a different vibration pattern, and/or switch to a particular pattern desired by the user or recommended by the other device, among other instructions. The interface 410 can be a wired or wireless interface, such as a wireless transceiver that transmits control signals between the personal massage apparatus and a second device. A skilled artisan will be able to select a suitable interface based on various considerations, including the device with which the personal massage apparatus will communicate and the size and shape of the main body. In some embodiments, the interface is a radio-frequency ("RF") transceiver used to transmit and receive RF signals between the personal massage apparatus and other devices. One example of an RF transceiver that could be used is a low power 2.4 GHz RF transceiver. In various embodiments, the personal massage apparatus may also include antennas for transmitting and receiving signals between die personal massage apparatus and other devices. In such examples, the interface can use BLUETOOTH®, Wi-Fi, infrared, laser light source, visible light source, acoustic energy, or one of a number of other methods to transmit information wirelessly between the personal massage apparatus and another device.

Figure 12:
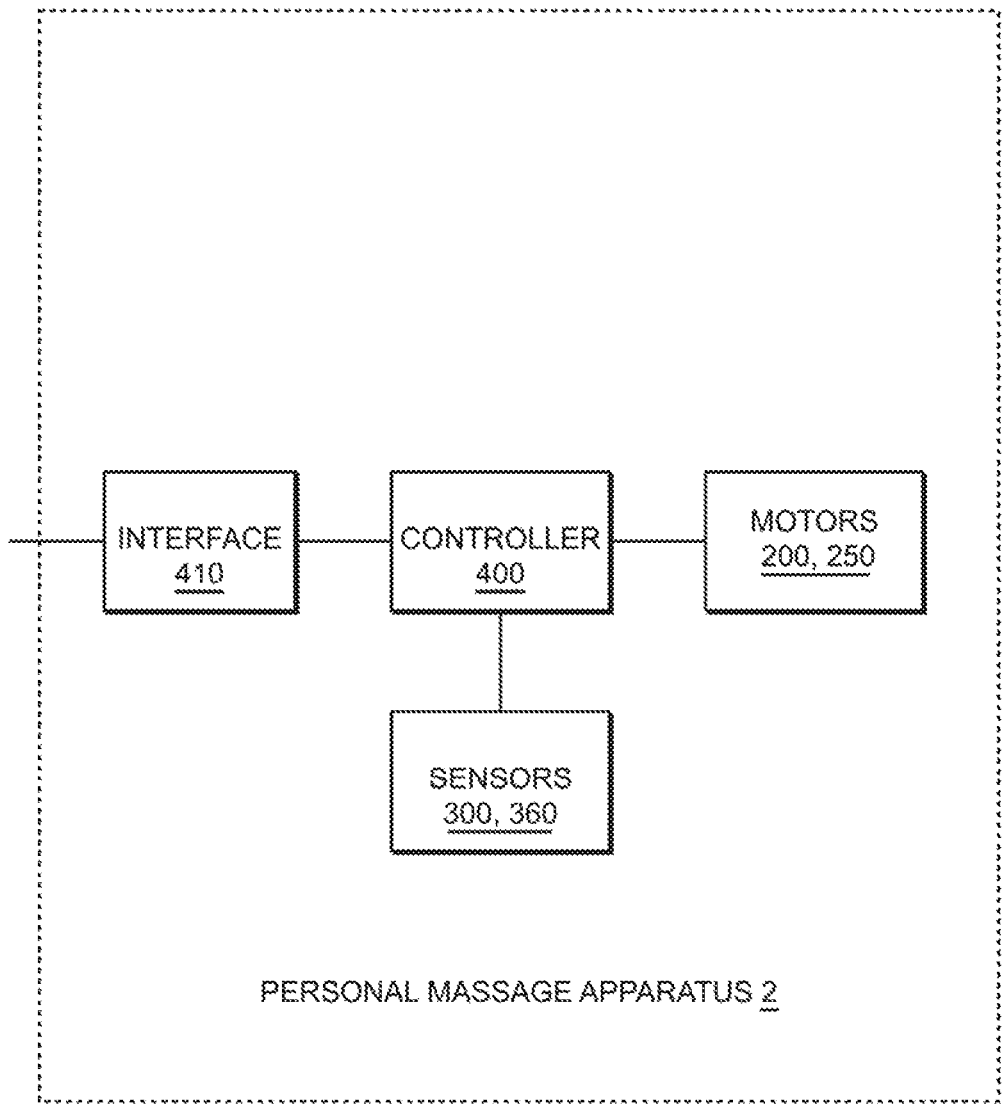
FIG. 12 is a diagram illustrating components of a networked personal massage apparatus in an example embodiment.

In some embodiments, the personal massage apparatus is connected to a network via the second device. In other embodiments, the personal massage apparatus is directly connected to a wireless router or cellular phone network and may connect with the second device in any of said manners. Accordingly, the personal massage apparatus can be controlled via personal computer, tablet, mobile phone, or other suitable electronic devices a user using the personal computer, tablet, phone, or other device in various embodiments. FIG. 12 illustrates one example of such a design.

FIG. 12 is a diagram illustrating component of a networked personal massage apparatus, such as personal massage apparatus 2, in accordance with an example embodiment. In this embodiment, the personal, massage apparatus 2 includes a controller, such as controller 400, one or more motors, such as first and second motors 200, 250, one or more sensors, such as the first 300, second 330, and third sensors and an interface, such as interface 410. As explained above, the personal massage apparatus can be connected to a network via a personal computer, tablet, mobile telephone, or other electronic device or can be directly connected to a wireless router or cellular phone network. Thus, as stated, the personal massage apparatus can be controlled by, transmit data to, and/or receive data from the personal computer, tablet, mobile telephone, or other electronic device via the aforementioned mechanisms. A skilled artisan will be able to determine how to suitably connect the personal massage apparatus with other devices based on various considerations, including the desirability of doing so and the devices to which connection would be beneficial. In some embodiments, the personal massage apparatus may not include an interface and, thus, may not communicate with other devices. In different embodiments, the personal massage apparatus may only transmit data to other devices; it may not receive any data and cannot be controlled via said other devices in this embodiment.

The main body 10 also houses the battery 450. The battery 450 is disposed adjacent the second end 14 of the main body 10 and is disposed closer to the endpiece 108 than is the distal end 34 of the sheath 30. The battery 450 is operatively connected, to the charging port 118 disposed on the endpiece 108. The battery 450 provides power to and is electrically coupled to at least the first and second motors 200, 250, the first 300, second 330, and third, sensors and the controller 400. The battery 450 comprises a lithium-ion battery in the illustrated embodiment and is rechargeable. The battery 450 is charged through the charging port 118, which is disposed beneath an optional cover 118a in this embodiment. A skilled artisan will be able to select a suitable battery and place it at a suitable position within the mam body according to a particular example based on various considerations, including the desired strength of the motors and the size and shape of the main body. In other embodiments, the battery may comprise a lithium battery, a NiMH battery, or some other type of rechargeable battery. In an alternative embodiment, the battery may not be rechargeable and, instead, may be replaceable. In a different embodiment, the personal massage apparatus may comprise more than one battery.

The battery 450 has the ability to hold a certain amount of energy to use upon the detection of a certain condition (hereinafter, "reserve power"). More specifically, the battery 450 is configured to maintain a certain amount of reserve power that it may distribute to the first motor 200 after the first sensor 300 detects a decrease in the rate of rotation of the drive shaft 402 in order to keep the motor 400 functioning during such periods when a load is placed on the personal massage apparatus 2. A skilled artisan will be able to select a suitable amount of energy comprising reserve power according to a particular example based on various considerations, including the desired strength of the motor and the size and shape of the housing. In one embodiment, the battery may store reserve power comprising between, about 1% and about 50% of the battery's total storage capacity. In another embodiment, the battery may store reserve power comprising between about 10% and about 35% of the battery's total storage capacity. In yet another embodiment, the battery may store reserve power comprising between about 15% and about 25% of the battery's total storage capacity. In a different embodiment, the battery does not store reserve power.

Figure 8:
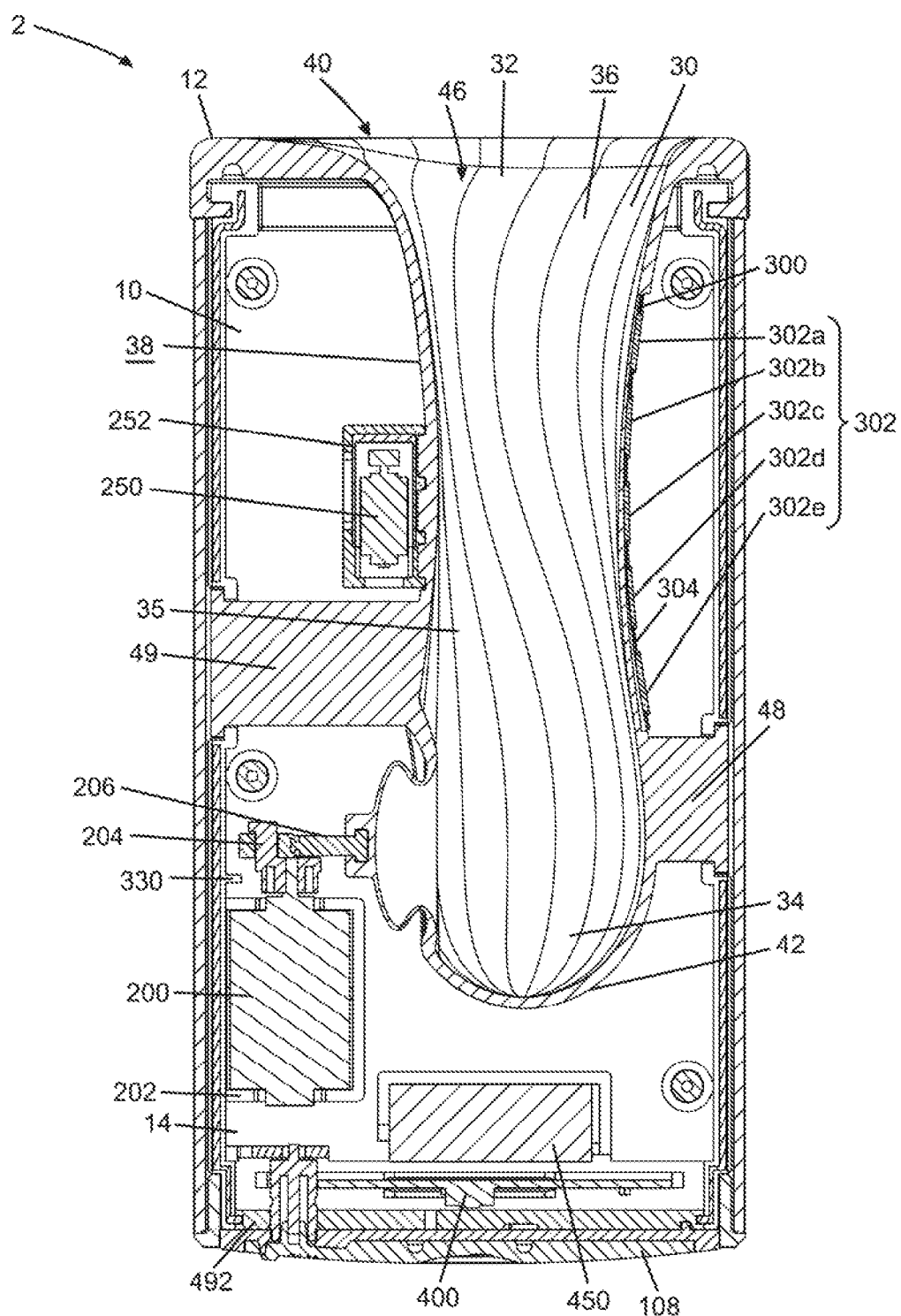
FIG. 8 is a cross-sectional view of the personal massage apparatus illustrated in FIG. 6, taken along line 8-8.

The first motor 200 is best illustrated in FIG. 8. The first motor 200 is disposed within the cavity 20 of the main body 10 and is disposed substantially adjacent the second end 14 of the main body 10. The first motor 200 is, therefore, also substantially adjacent the distal end 34 of the sheath 30 such that, when in operation, the first motor 200 provides stimulation to the tip, head, and/or end of the penis of a user. The first motor 200 includes a housing 202 that holds the first motor 200 in place within the main body 10, as well as a earn 204 and rod 206 that aid in production and transmission of vibrations and pulsations. The rod 206 extends toward the distal end 34 of the sheath 30 and contacts the outer surface 38 of the same to provide stimulation to the penis disposed within the chamber 46. A magnetic unit (not illustrated in the Figures) is attached to the rod 206. Accordingly, when the first motor 200 is in operation, the movement of the rod 206 produces stimulating waves that axe transmitted into the chamber 46. In combination or sequence, the stimulating waves comprise stimulation patterns that are transmitted to the penis disposed within the sheath 30.

The first motor 200 operates such that the rod 206 rotates in place about its longitudinal axis (not illustrated in the Figures), which extends along the length of the rod 206 through its center; these rotations generate stimulating waves, which comprise the various patterns. Based on the particular pattern of rotations of the rod 206, the stimulation patterns may be constant or varying; they may also comprise bursts or vary in intensity and/or duration. The controller 400 transmits a user's selection of stimulation patterns to the first motor 200, which then implements such selections. A skilled artisan will be able to select a suitable first motor according to a particular example based on various considerations, including the placement of the first motor relative to the portion of the device configured to emit stimulation and the types of stimulation patterns that the device is designed to emit. In some embodiments, the first motor may comprise an electric motor, in other embodiments, the rod may rotate at any rate, including between about 1,000 revolutions per minute ("rpm") and about 5,000 rpm, between about 2,000 rpm and about 4,000 rpm, and between about 2,500 and about 3,500 rpm. In other embodiments, the magnetic unit may be attached to the rod through any mechanical means or through an adhesive; it may also be disposed within the rod. In various embodiments, the magnetic unit may comprise one, two, three, or more than three individual magnets. In other embodiments, the first motor may comprise an oscillation motor.

Depending on the particular types of stimulating waves that are emitted, the first motor 200 may produce a vacuum (or partial vacuum) within the chamber 46, which produces a suction-like effect on the user when a part of the user's penis is partially or tally disposed within the chamber 46. A vacuum is especially likely to occur when the personal massage apparatus 2 is in use and the user's penis is thick and/or large enough to create a seal at the one or both of the openings 18, 40 of the proximal end 32 of the sheath 30 and/or first end 12 of the main body 10. In the event a seal is not created, the user will still receive a suction-like effect on his penis. The inner surface 36 of the sheath 30 is designed such that it can act as a diaphragm and, in some instances, similar to a speaker configured to emit audio; thus, it may be disposed slightly closer to the penis when the first motor 200 is in use as compared to when it is not in operation. The first motor 200 may be configured to produce other stimulating waves and stimulation patterns, as well. In addition, the personal massage apparatus 2 may be configured such that when the waves produced by the fist motor 200 are transmitted toward the portion of the user disposed within the chamber 46, the waves and/or vibrations may reflect after contacting the user, contact the inner surface 36 of the sheath 30 again, and then reverberate towards the user. This would provide added stimulation to a user that would be unpredictable, as the reverberating waves would not behave in a consistent manner. A skilled artisan will be able to select a suitable first motor according to a particular example based on various considerations, including the placement of the first motor relative to the sheath and the types of stimulation patterns that the apparatus is designed to emit. In other embodiments, the first motor may only produce stimulating waves that produce a suction-like effect within main body. In different embodiments, the first motor may only produce stimulating waves that produce expulsion of air from the chamber of the main body. In an alternative embodiment, the first motor may be configured to vibrate and/or pulsate without suction or the expulsion of air. In various embodiments, the first motor may produce suitable vibrations and/or pulsations having frequencies between about 10 Hertz (Hz) and about 150 Hz, between about 40 Hz and about 120 Hz; and about 70 Hz and about 90 Hz. In additional embodiments, the first motor may pulsate between about 500 and about 5,000 times per minute, between about 5,500 and about 4,000 times per minute, and between about 3,200 and about 3,800 times per minute. In other embodiments, the apparatus does not produce a vacuum and instead merely stimulates a user via the production of waves, pulsations, and/or vibrations.

The second sensor 330 is disposed within the main body 10 and adjacent the first molar 200 on the interior surface of the middle portion 16. FIG. 8 most clearly illustrates the second sensor 330. The second sensor 330 is configured to detect how frequently the rod 206 rotates in u given period of time by monitoring the number of times the magnetic unit moves past the second sensor 330. Any suitable second sensor may be used in various embodiments, so long as the sensor can detect the position of the magnetic unit over time and transmit such information to the controller. A Hall Effect Sensor (sometimes referred to as a Hall Sensor) is a suitable example of such a second sensor.

When a load, such a user pressing the first end 12 of the main body 10 to his body with a strength that passes a certain threshold, is placed upon the personal massage apparatus, the first motor 200 slows and the rod 206 (and, thus, the magnetic unit) rotates less quickly. The second sensor 330 detects the lower rate of rotation of the magnetic unit in a given time period, indicating that the number of rotations of the rod 206 in a given time period has decreased. Upon sensing the changes to the rate of the rotation of the rod 206, the second sensor 330 alerts the controller 400 of the reduced rate of rotation of the rod 206; the controller 400 then instructs the first motor 200 to increase production and the battery 450 to provide the first motor 200 additional energy to do so (as described above). Alternatively, the second, sensor 330 can directly Instruct the first motor 200 to increase output in response to fee load exerted on the first end 12 by the user that has slowed the rod 206.

Upon such an instruction from the second sensor 330 or the controller 400, the first motor 200 will use reserve energy that is stored by the battery 450 to maintain the output of the first motor 200. The battery's 450 capability of holding such reserve, power is described above. This allows the user to continue to receive, for a period of time, the same stimulation pattern that is generated when the second sensor 330 does not sense any change in the fate of rotation of the rod 206 due to contact with a user. Therefore, the rod 206 maintains the ability to rotate at the same rate as when there is no load on the personal massage apparatus 2 based on the second sensor's 330 output for a period of time. A skilled artisan will be able to determine what type of second sensor to use and where to place the second sensor according to a particular example based on various considerations, including the size and shape of the first motor and the type of second sensor used. In different embodiments, the second sensor may be disposed at any suitable portion within the main body and h may be configured to measure the rate of relations of the rod in any suitable manner. In other embodiments, the second sensor may be adjacent to the second motor. In various embodiments, the second sensor may have any particular sensitivity level (i.e., extremely, moderately, or minimally responsive to change in rod rotation) and may act on a delay prior to instructing the motor to increase output.

The second sensor 330 may also be configured to measure the thickness and/or circumference of the penis of a user and transmit the same to a second device. By measuring how, when, and if a vacuum and/or seal is generated during use, the second sensor 330 can determine whether the user has a penis having a circumference and/or thickness that is small, medium, or large, as compared with a database relating to penis circumference and/or thickness that is stored on a software application on a second device. In some embodiments, the second sensor may be equipped to measure the actual circumference or width of the penis, rather than provide a general measurement of size. A skilled artisan will be able to select how to suitably configure a second sensor to measure penis thickness and circumference according to a particular example, including the sensitivity of the second sensor and the material comprising the sheath. In some embodiments, the penis thickness and/or circumference may include additional categories, including extra small, extra-large, and any other suitable categories.

The second motor 250 is disposed within the main body 10 and adjacent the middle portion 35 of the sheath 30. More specifically, the second motor 250 is disposed adjacent the second support column 49 and is disposed nearer to the proximal end 32 of the sheath than is the first motor 200. The second motor 250 includes a housing 252 configured to maintain the second motor 250 at a stable position within the cavity 20 of the main body 10. When in operation, the second motor 250 provides stimulation to the shaft of the penis of a user. The second motor 250 is an oscillating motor in this embodiment and may be used in conjunction with or separately from the first motor 200. In the illustrated embodiment, the first and second motors 200, 250 may vibrate, pulsate, or otherwise produce stimulations that act cooperatively to increase stimulation to the user (such as by vibrating or pulsating in synchronization). They may also negatively impact total stimulation produced when they are in operated together by vibrating or pulsating at different frequencies or wavelengths from one another. The second motor 250 can produce one or more of stimulating waves, vibrations, and pulsations and may vibrate constantly, pulse on a particular pattern, pulse randomly, and otherwise provide stimulation in a variety of manners. Any suitable motor may comprise the second motor. A skilled artisan will be able to select a suitable second motor according to a particular example based on various considerations, including the placement of the second motor relative to the sheath, the placement of the first motor, and the types of stimulation patterns that the apparatus is designed to produce. In other embodiments, the second motor may produce stimulating waves that produce a suction-like effect within main body or stimulating waves that "push" air from within the chamber through and out of its opening. In various embodiments, the second motor may produce suitable vibrations and/or pulsations having frequencies between about 10 Hz and about 300 Hz, between about 50 Hz and about 150 Hz, and about 70 Hz, and about 90 Hz. In some embodiments, the second motor operates at a higher frequency than does the first motor; in other embodiments, the first motor operates at a higher frequency than does the second motor. In additional embodiments, the second motor may pulsate between about 500 and about 15,000 times per minute, between about 3,000 and about 12,000 times per minute, and between about 9,000 and about 11,000 times per minute.

The main body 10 also houses the first sensor 300. The first sensor 300 comprises a capacitive sensor and includes a set of nodes 302, including first, second, third, tour, and fifth nodes 302a, 302b, 302c, 302d, 302e, respectively (collectively referred to as "the nodes 302"). The nodes 302 are disposed on a sensor unit 304, which also comprises a portion of the first sensor 300. The first sensor 300 is attached to the outer surface 38 of the sheath 30 and extends along the sheath 30. More specifically, each of the nodes 302 of the first sensor 300 are spaced from one another along the length of the middle portion 35 of the sheath 30. The first node 302a is disposed more closely to the proximal end 32 of the sheath 30 than is any other node 302, while the fifth node 302e is disposed more closely to the distal end 34 than is any other node 302. The first sensor 300 is disposed closer to the proximal end 32 of sheath than are either of the first support column 48 or second support column 49. This placement of the nodes 302 aids in collecting data related to the length and shape of the penis of a user. It also allows the first sensor 300 to measure movement of the penis while it is within the sheath 30, as described below. Further, the sensor 300 is disposed substantially opposite the second motor 250 on the outer surface 38. A skilled artisan will be able to select a suitable first sensor according to a particular example based on various considerations, including, the number of desired nodes and what the skilled artisan wishes to measure. In another example, the sensor may include zero, one, two, three, four, six, seven, eight, or more than eight nodes. In a different example, the sensor may extend around the exterior of the sheath to form a ring, may be placed adjacent the tip of the sheath, may extend to the proximal end of the sheath, and may otherwise be placed as a skilled artisan sees fit.

The first sensor 360 is also configured such that when it (and, by extension, the sheath 30) comes in contact with or close proximity to the skin of a user, the first sensor 300 detects a change in capacitance due to said contact or close proximity and communicates said changes to the controller 400. The controller 400 operates one or both of the first and second motors 200, 250 in response to said changes. In conjunction, the first sensor 300 and the controller 400 are able to discriminate between an object with high water content (such as a human body) and other objects. Consequently, the first sensor 300 aids in preserving the life of the battery 450, as it will not operate without sensing close proximity to or contact with an object with high water content. The first sensor 300 may be comprised of any suitable material, including copper or indium tin oxide.

To sense activation of the first sensor 300, the controller 400 includes a relaxation oscillator, which generates a wave whose frequency changes along with the capacitance of the first sensor 300. More specifically, the frequency increases as the capacitance of the system increases and decreases as the capacitance of the system decreases. A counter measures the number of oscillations that occur during a fixed time period; when the number of oscillations during the time period falls below a set level indicating the presence of a body, the controller 400 registers the presence of a body. A body may sufficiently alter the capacitance of the first sensor 300 to reduce the number of oscillations below the level indicating a body even when the massager is not in actual contact with the body. Accordingly, the first sensor 300 can detect such changes in capacitance through the sheath 30; as such, it will still function even though it is disposed on the outer surface 38 of the sheath 30 and may not directly contact the skin of the user. The actual distance from the main body 10 that registers as the user's presence may vary. Regardless, proximity to or contact with a user is necessary for the personal massage apparatus 2 to operate. A skilled artisan will be able to select a suitable first sensor according to a particular example based on various considerations, including the types and strengths of first and/or second motors and the desired sensitivity of the first sensor. In various embodiments, the first sensor may be comprised of any suitable material. In different embodiments, the first sensor may be configured such that a user must be in direct contact with the sheath and/or main body in order for the first and/or second motor to operate. In other embodiments, the distance from the sensor, sheath, and/or main body from which the first sensor registers the presence of the body of a user may include a millimeter, a centimeter, an inch, or more than an inch.

The first sensor 300 is configured to collect various measurements relating to a user's use of the personal massage apparatus 2 and transmit the same to the controller 400, which then can be transmitted to a second device, such as a mobile phone, as described above. For example, the first sensor can 300 can collect data related to the length of the penis of the user by measuring which of the nodes 302 of the first sensor 300 are most closely adjacent the tip of the penis of a user. As described below, the tip of the penis extending to a particular node 302 will correspond with a particular penis length. The sensor 300 is sufficiently capable of measuring capacitance such that it will be able to differentiate when the tip of the penis extends, for example, only to the third node 302c but does not extend to the fourth node 302d.

The first sensor 300 also measures the frequency of penile insertions or motions toward and away from the distal end 14 (i.e., thrusts) during a session. In one example, the frequency may be measured by the total number of times the penis is adjacent the first node 302a, but not any other nodes 302, over a period of time; this information would be sent to second device which would calculate the number of insertions, during a session. In another example, the number of times the tip of penis is adjacent the fourth node 302d could be measured (assuming the length of the penis does not extend to the fourth node 302d while not in motion). This information would be sent to a second device to calculate the repetitions of a particular motion of the personal massager towards and away from the user during a session. The first sensor may also record data of a second session for transmission to a second device for comparison with the data recorded in a first session. The first sensor 300 can also measure the total duration of a session.

Any data related to the length of the penis, frequency of insertions and/or motions, and other similar movements may be measured by the first sensor in other embodiments, as well. A skilled artisan will be able to select data for the first sensor to measure according to a particular example based on various considerations, including the type and sensitivity of the first sensor and the intended use of the apparatus.

The personal massage apparatus 2 also includes a third sensor (not illustrated in the Figures) configured to detect orientation and movement of the personal massage apparatus 2. The third sensor comprises a portion of the controller 400 and comprises a gyroscope sensor (and accelerometer) that is intended to measure orientation and movement of the personal massage apparatus on three axes: the x-axis (i.e., towards and away from the body of the user), the y-axis (i.e., towards the user's left side and right side, and the z-axis (towards the user's head and his feet). In simpler terms, the third sensor can detect orientation positions that include left, right, up, down, back, and front. Accordingly, the third sensor can detect the orientation and movement of the personal massage apparatus 2 relative to the user and transmit said information to the controller 400 and/or second device, such as a mobile phone. The third sensor can measure both the speed and direction of the personal massage apparatus 2 over time. In various embodiments, any gyroscope sensor and/or accelerometer may comprise the third sensor. For example, a gyroscope sensor such as a microelectromechanical systems ("MEMS") gyroscope may be used; MEMS gyroscopes are commonly used in mobile phones and other electronic devices. Other vibrating structure gyroscopes can be used, as well.

Data that the third sensor may measure, collect, and/or transmit includes the rate and direction of movement of the personal massage apparatus 2. By measuring the position of the third sensor over time, the rate of movement of the personal massage apparatus 2, and thus the user's hand, can be calculated. Most commonly, the third sensor will measure the movement of the personal massage apparatus 2 towards and away from a user's body along the length of the penis, though it can also measure other patterns of movement.

The third sensor may also measure, collect, and transmit data relating to the direction in which the personal massage apparatus 2 moves and/or is oriented. Such data may include the angles at which the personal massage apparatus moves relative to the body, the various changes in direction of the personal massage apparatus 2 along the three aforementioned axes that a user Initiates, the various orientations of the personal massage apparatus 2 during a session, and the patterns that a user prefers along such axes. In some embodiments, the third sensor will be able to detect whether a user is using his right or left hand, depending on the changes in speed and/or direction of the personal massage apparatus detected by the third sensor.

In various other embodiments, one or more of the first, second, and/or third sensors may measure, collect, and/or transmit additional data to the controller and/or a second device. A skilled artisan will be able to select suitable additional types of data to be collected according to a particular example based on various considerations, including the size and shape of the personal massage apparatus and the particular first, second, and third sensors used. In one embodiment, a sensor may detect audio and determine how much and what noises a user makes while using the device. In another embodiment, a sensor may be configured to detect pulsations of the penis. In a different embodiment, a sensor may communicate with a smartwatch to track a user's pulse while be uses the personal massage apparatus. In other embodiments, the third sensor may only detect movement on one or two axes, rather than three. In a different embodiment, the third sensor may only comprise an accelerometer. In an alternative embodiment, one or both of the first and second motors may increase or decrease in output based on one or more orientations sensed by the third sensor. The third sensor may detect orientation on various planes, as well.

Optionally, and as is illustrated in FIGS. 8 and 9, the personal massage apparatus 2 may include one or more light sources 490, 492. The first light source 490 is disposed within the main body 30 along the inner surface of the middle portion 16. The first Sight source 490 comprises an LED light configured to illuminate the cavity 20 when the personal massage apparatus 2 is in use. More specifically, the first light source 490 helps a user see into the main body 10 through the viewing panel 120 in order to see the components stored within the same. The first light source 490 may emit light of any color, including one or more of blue, green, orange, red, purple, yellow, white, or any other suitable light color.

The second light source 492 is disposed adjacent the endpiece 108 of the shell 100. The second light source 492 is configured to illuminate the distal end 104 and endpiece 108 such that a colored ring is found around the endpiece 108 when the personal massage apparatus 2 is in use. Optionally, the second light source 492 may be positioned such that it illuminates the first, second, and third 112, 114, 116 user controls when the personal massage apparatus 2 is in use. Such an alignment would aid a user in viewing the first, second, and third 112, 114, 116 user controls in the dark. The second light source 492 may emit light of any color, including one or more of blue, green, orange, red, purple, yellow, white, or any other suitable light color. A skilled artisan will be able to select suitable first and second light sources according to a particular example based on various considerations, including the size and shape of the personal massage apparatus and whether a viewing panel is present. In other embodiments, other light source sources may be used in place of LED light sources. In a different embodiment, zero, one, three, or more than three light sources may be included.

As described above, the data collected by the first, second, and third sensors 300, 330 may be transmitted to a second device (not illustrated in the Figures) via the controller 400. As was also described above, the data, may include data related to one or more of: the user's penis length, width, or circumference; the frequency of insertions, motions or thrusts by the user over a period of time; the duration of one or more sessions; the user's pulse; the user's speed and direction of use of the personal massage apparatus on three axes; the position of the personal massage apparatus over time; the rhythms and/or patterns of use; and/or sounds produced by the user during use. Alter transmission of this data to a second device, such as a mobile phone having a software application configured to store and analyze this data, the second device can log both data from individual, sessions and average data generated across multiple sessions. The data may also include maximum data for a particular measurement (i.e., longest duration, date on which, the penis had the most circumference, etc.). The software may also compare the lengths, circumferences, and widths of a user's penis to other users' lengths circumferences and widths or a data set containing average measurements for the same. This data can then be displayed to the user on a display of the second device; an example of such a display is a screen of a mobile phone.

Additionally, upon receipt of the data, the software application can analyze the data and provide suggestions, tips, and other advice to the user to improve the user's sexual performance. Such suggestions, tips, and advice may include, but is not limited to: preferable angles, durations, speeds, positioning, rhythm, thrusts, and motions that a user may practice. These will both improve the pleasure experienced by the user while using the personal massage apparatus and aid a user when he is having sexual intercourse with another person. More specifically, the software application will provide suggestions, tips, and advice based on satisfactory sexual performance techniques. For example, the software application may provide advice regarding how long a session should last, the motions and/or insertion patterns and rhythms preferred by various sexual partners (these could differ based on whether a preferred, partner is a man or woman), and various the speed and direction of movement that may be pleasurable to others.

Optionally, the personal massage apparatus may be controlled remotely by the mobile phone via the software application. In one such example, the personal massage apparatus may control, one or both of the motors, dictate what is measured by the sensors, control the emission of light by the light sources, and control a particular pattern of stimulation emitted, by the personal massage apparatus. Remote control would be particularly advantageous if the user is physically separate from his preferred partner.

The software application may be open source in some embodiments, as well. That is, users and others that have the capability of programming the software application may add their own code to the software application. Such code may one or both of the motors, dictate what is measured by the sensors, control the emission, of light by the light sources, and control a particular pattern of stimulation emitted by the personal massage apparatus. A skilled artisan will be able to suitably configure a second device having a software application according to a particular example based on various considerations, including the intended user of the apparatus and what data is to be collected. In some embodiments, the software may only display one or more of the aforementioned data sets. In different embodiments, the software may be open or closed source.

The personal massage apparatus 2 can foe used in various ways. The following is one such example.

In use, a user will insert his penis into the sheath 30 such that the tip of his penis is closer to the distal end 34 than the proximal end 32. Next, the user will activate the software application on a second device, such as a mobile phone, and ensure that the software application is ready to receive and analyze data from the personal massage apparatus 2. A user will then activate the personal massage apparatus 2 via the first user control 112. Activation will power on the personal massage apparatus 2, which will include operation of the first and second motors 200, 250 and, optionally, illumination of the personal massage apparatus 2 via the first and second light sources 490, 492. A user then, optionally, may increase or decrease the intensity of the vibrations and/or pulsations of the personal massage apparatus 2 via the second and third user controls 114, 116. The intensity may be adjusted at any point during use. The user will then thrust, move, remove and reinsert, position, and otherwise use the apparatus as described above. Most commonly, a user will move the personal massage apparatus 2 along the length of his penis such that the penis is stimulated by the first and second motors 200, 250 and the inner surface 36 of the sheath 30. While the user is using the personal massage apparatus 2, the first 300, second 330, and third sensors will collect the data described above and transmit the same to a second device via the controller 400 and/or interlace 410. Eventually, the user will stop using the personal massage apparatus 2; most commonly, a user will cease using the same after be has ejaculated and/or climaxed, whether within the sheath 30 and/or main body 10 or outside of the same. A user, then, will access the software application on his second device to review the data collected, by the personal massage apparatus 2 during the session. He will then be able to access the various suggestions, tips, and advice as to how to improve his sexual performance and increase sexual pleasure to both himself and others, whether or not he is using the personal massage apparatus 2.

FIGS. 13, 14, 15, 16, 17, 18, 19, 20, 21, 22, and 23 illustrate another example personal massage apparatus 4 configured to be used by men and/or various components thereof. The personal massage apparatus 4 is similar to the personal massage, apparatus shown in FIGS. 1 through 11, except as described below. Thus, the personal massage apparatus 4 comprises a main body 500, a shell 600, a first motor 700, a second motor 750, a first sensor 800, a second sensor 830, a third sensor (not illustrated in the FIGS.), a controller 900, a battery 950, and various other components that will be described in greater detail below.

The main body 500 of the personal massage apparatus 4 includes two pads 550, 552 disposed within the main body 500 in the illustrated embodiment. The pads 550, 552 are comprised of silicone and are attached to the interior surface 506. The pads 550,552 are disposed substantially adjacent the first end 502 of the main body 500 and are configured to reduce the noise generated by the second motor 750, which is disposed within and attached to a motor housing 752. The motor housing 752 and second motor 750 are disposed nearer to the first end 502 of the personal massage apparatus 4 than to its second end 504. The second motor 750 and the motor housing 750 may be secured in position within the main body 500 via any suitable mechanism. A skilled artisan will be able to select suitable pads according to a particular example based on various considerations, including the shape and size of the main body and the amount of cushion which the pads are configured to provide. In various embodiments, the pads may be attached to the main body via any mechanism, including a mechanical attachment and/or an adhesive. They may also be integrally formed with the main body. Furthermore, in other embodiments the personal massage apparatus may include zero, one, three, or more than three pads. The pads also may be comprised of any suitable material in different embodiments.

The first sensor 800 of personal massage apparatus 4 has eight nodes (not illustrated in the FIGS.) in this embodiment. These provides the first sensor 800 the ability to collect data in greater detail than would a sensor with fewer nodes.

Figure 13:
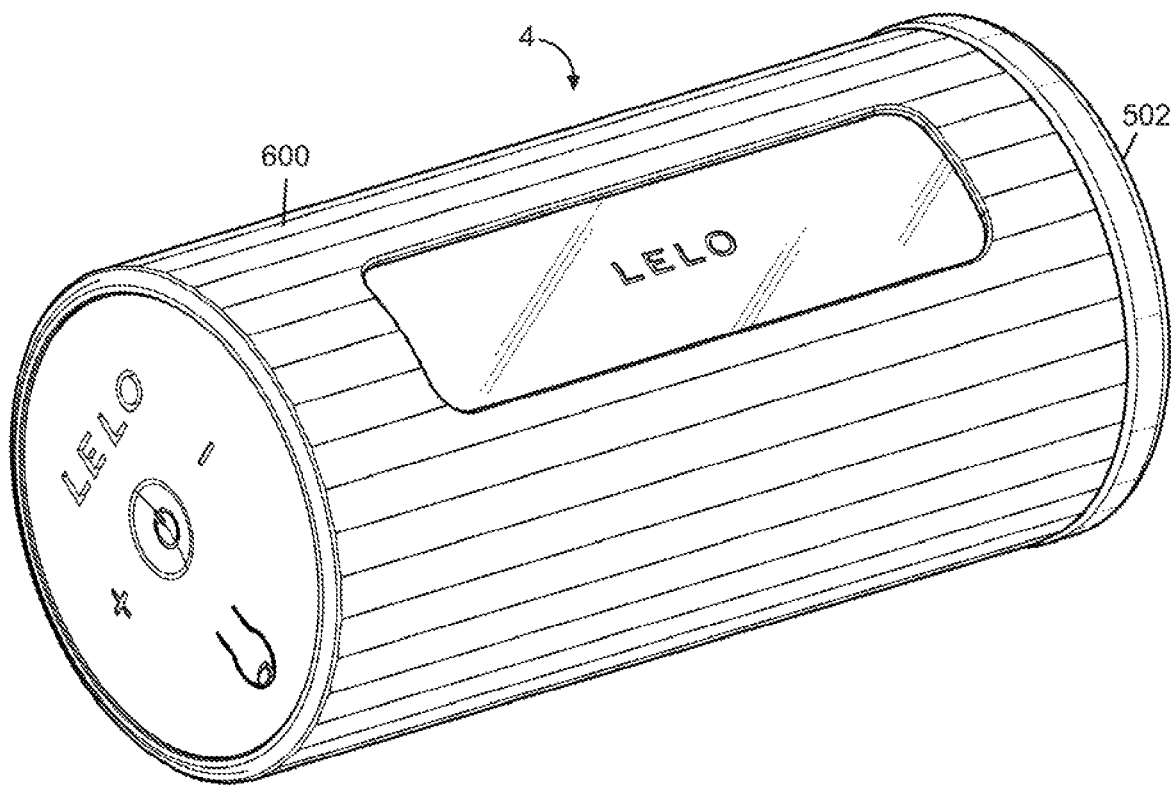
FIG. 13 is a perspective view of a second example personal massage apparatus.
Figure 14:
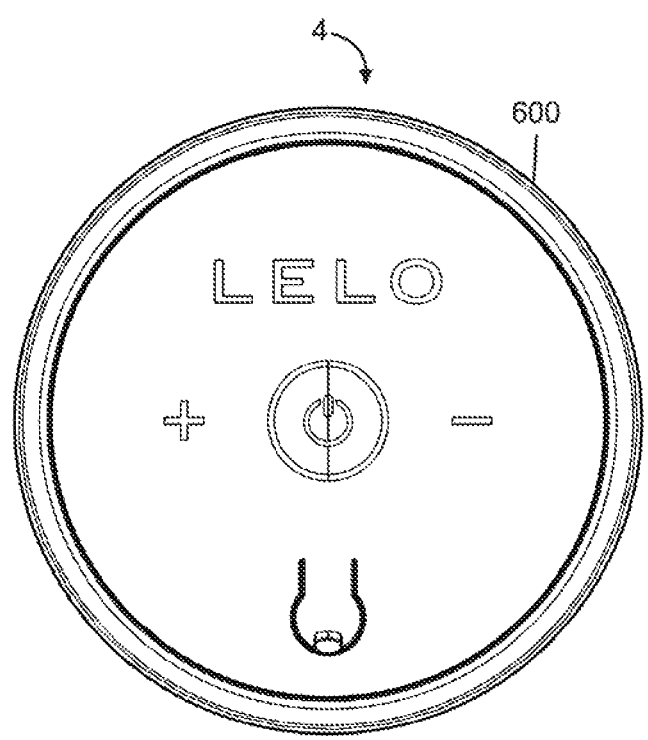
FIG. 14 is a bottom view of the personal massage apparatus illustrated in FIG. 13.
Figure 15:
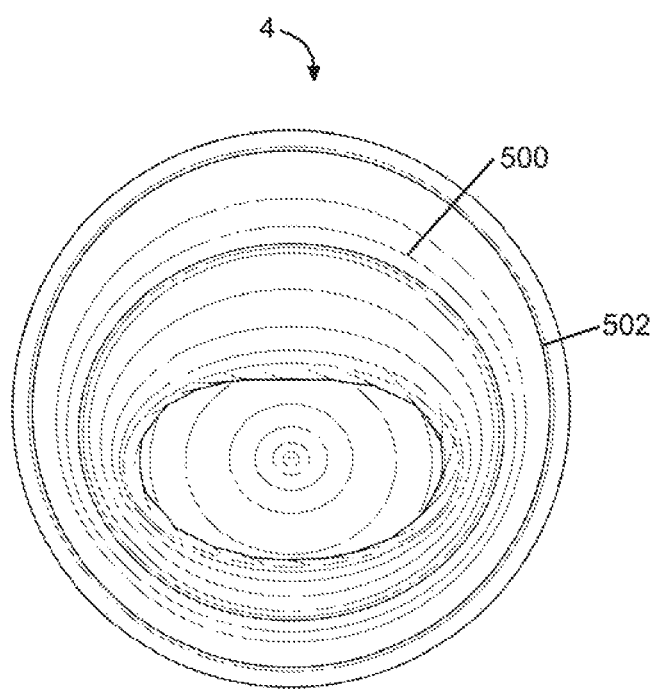
FIG. 15 is a top view of the personal massage apparatus illustrated in FIG. 13.
Figure 16:
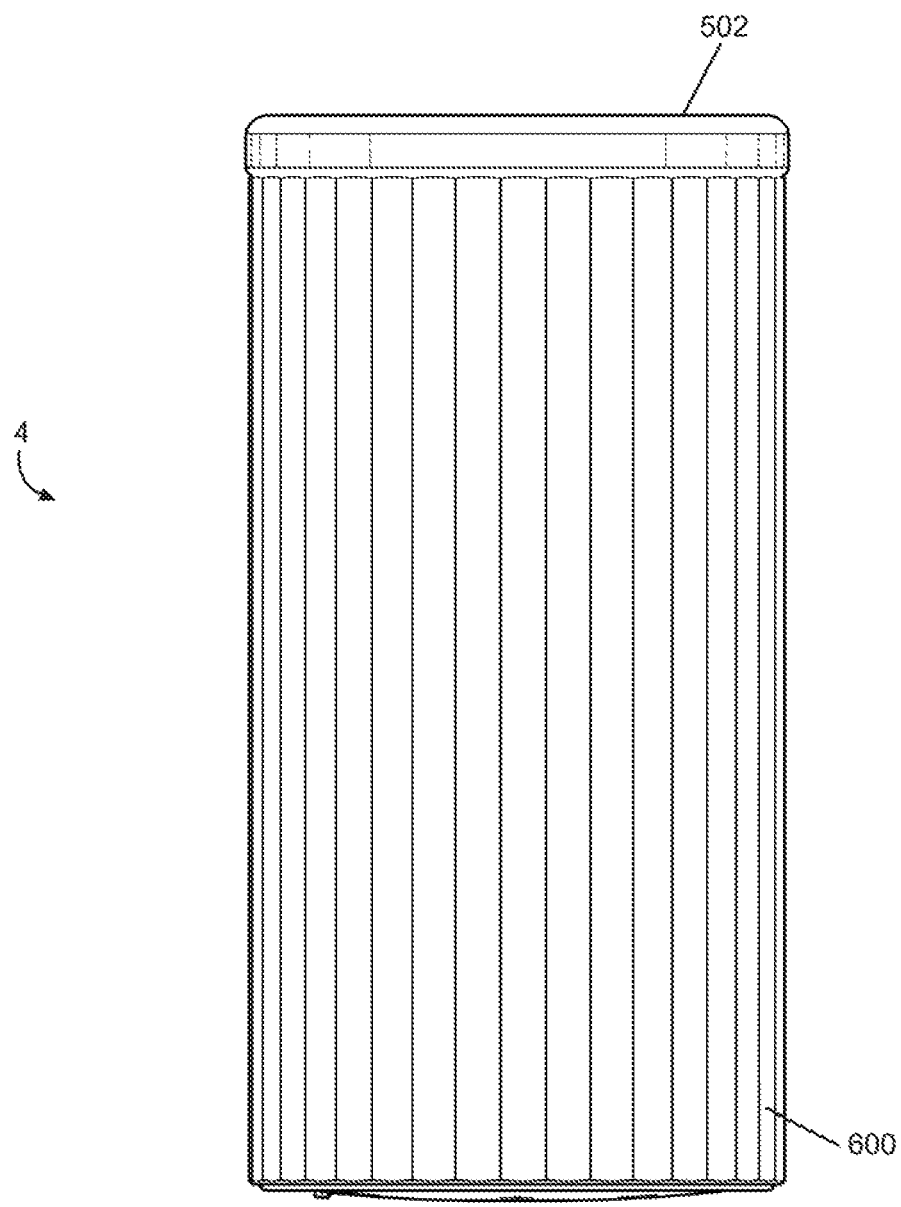
FIG. 16 is an end view of the personal massage apparatus illustrated in FIG. 13.
Figure 17:
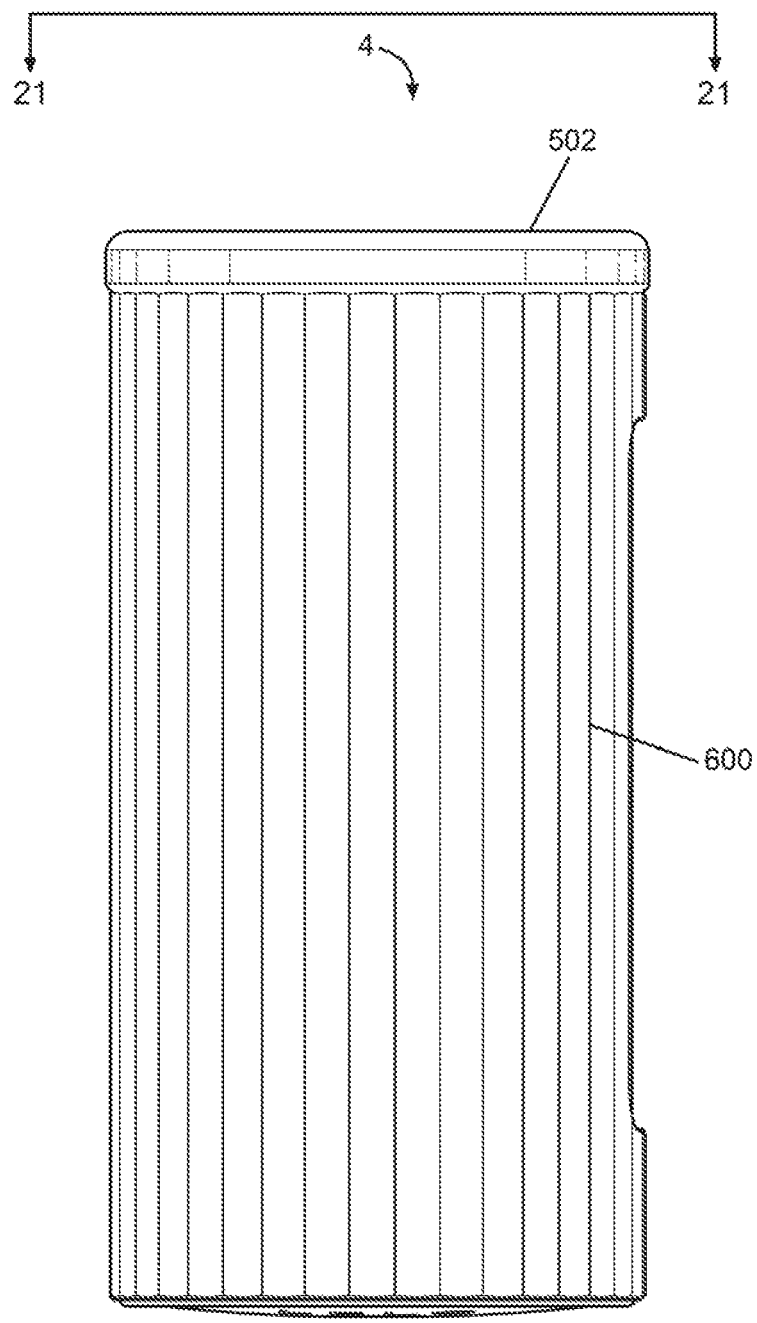
FIG. 17 is a side view of the personal massage apparatus illustrated in FIG. 13.
Figure 18:
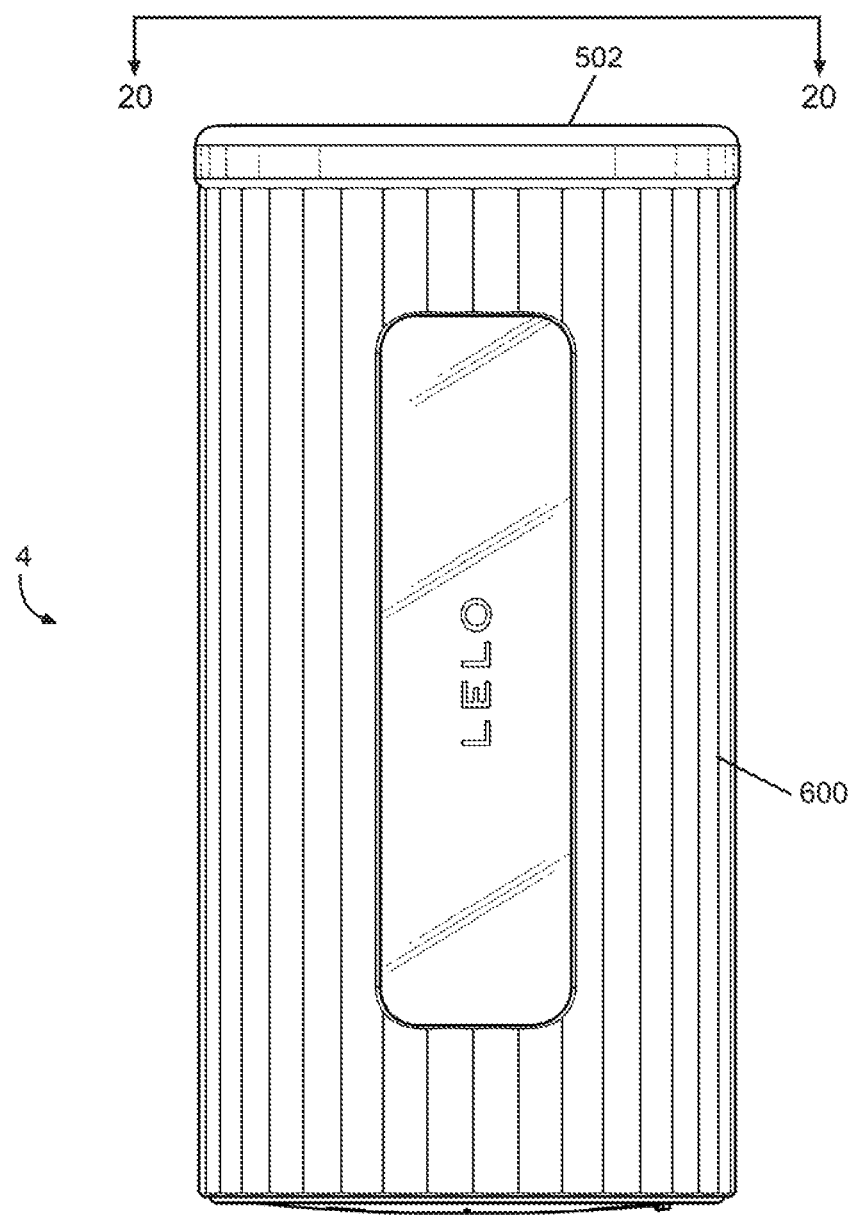
FIG. 18 is another end view of the personal massage apparatus illustrated in FIG. 13.
Figure 19:
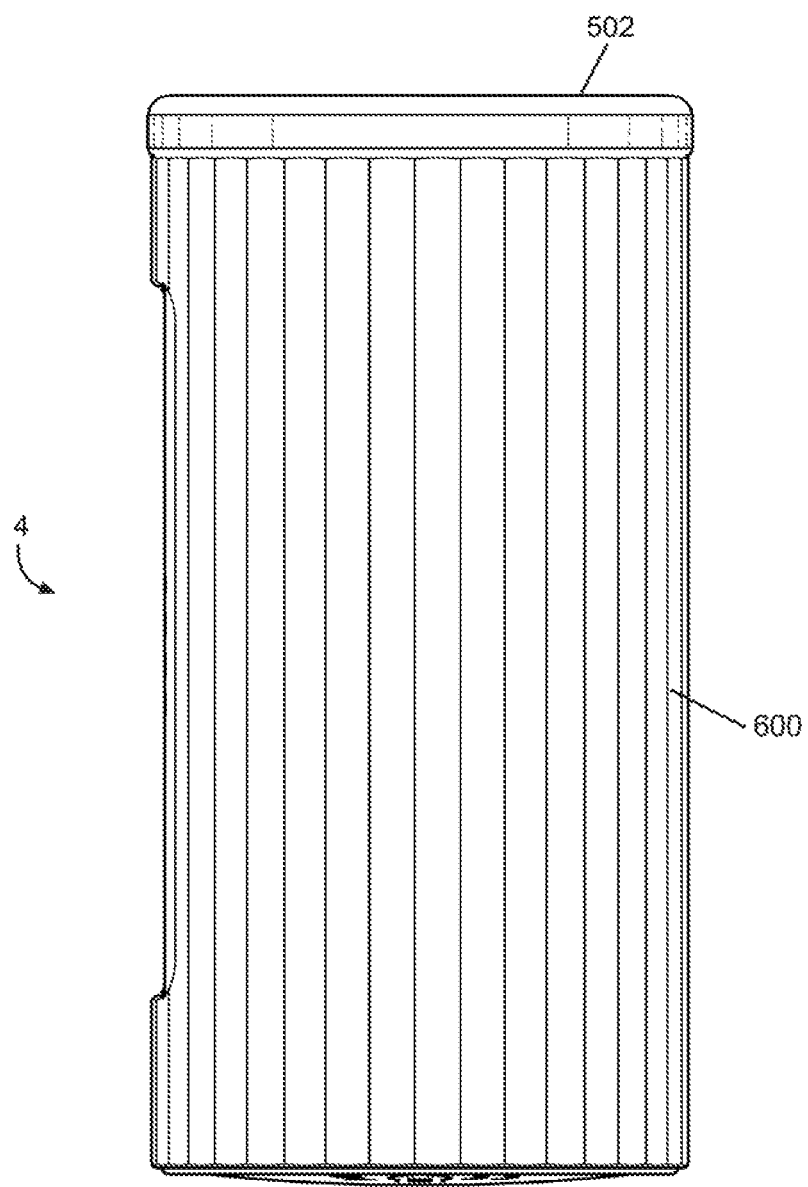
FIG. 19 is another side view of the personal massage apparatus illustrated in FIG. 13.
Figure 20:
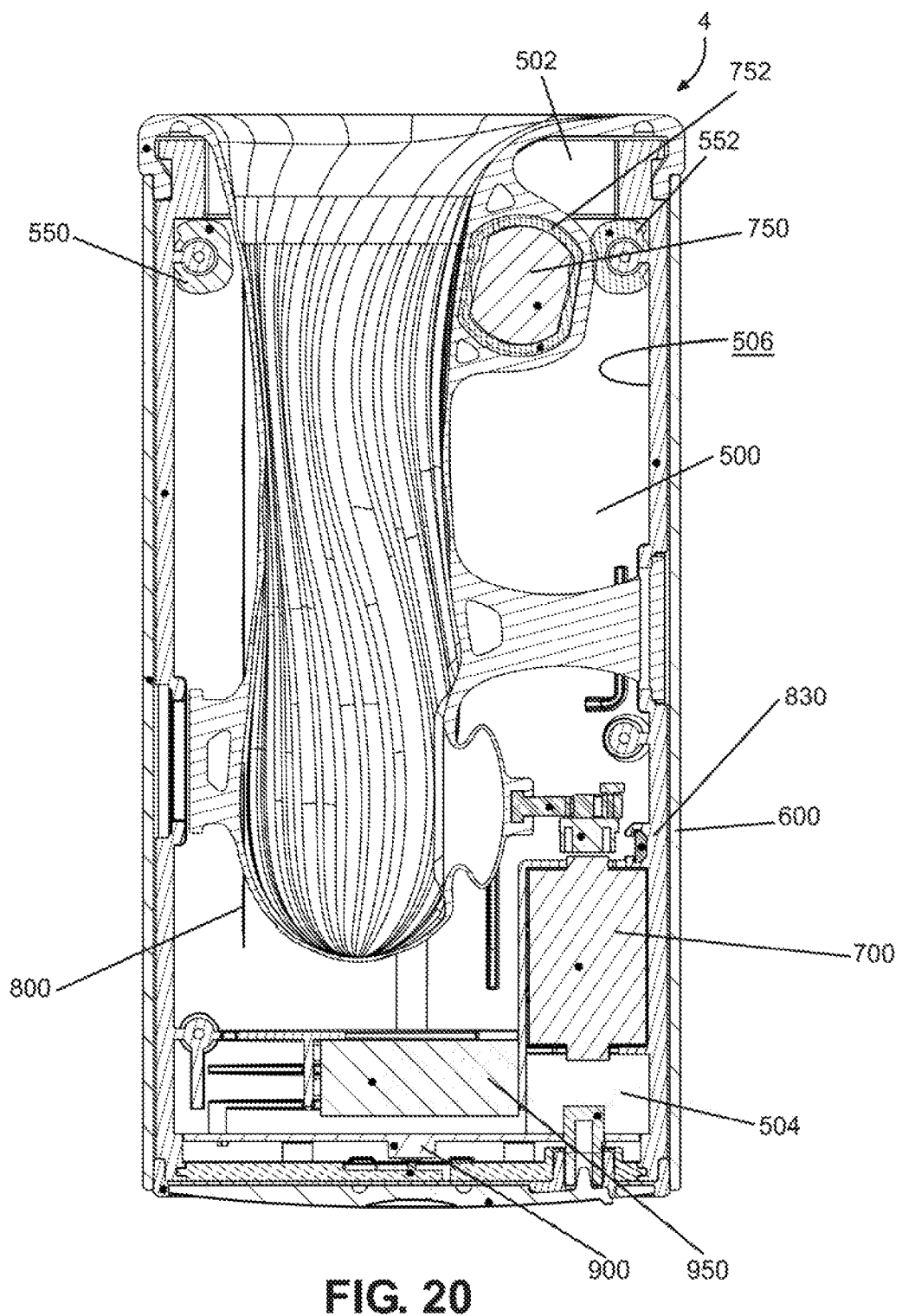
FIG. 20 is a cross-sectional view of the personal massage apparatus illustrated in FIG. 18, taken along line 20-20.
Figure 21:
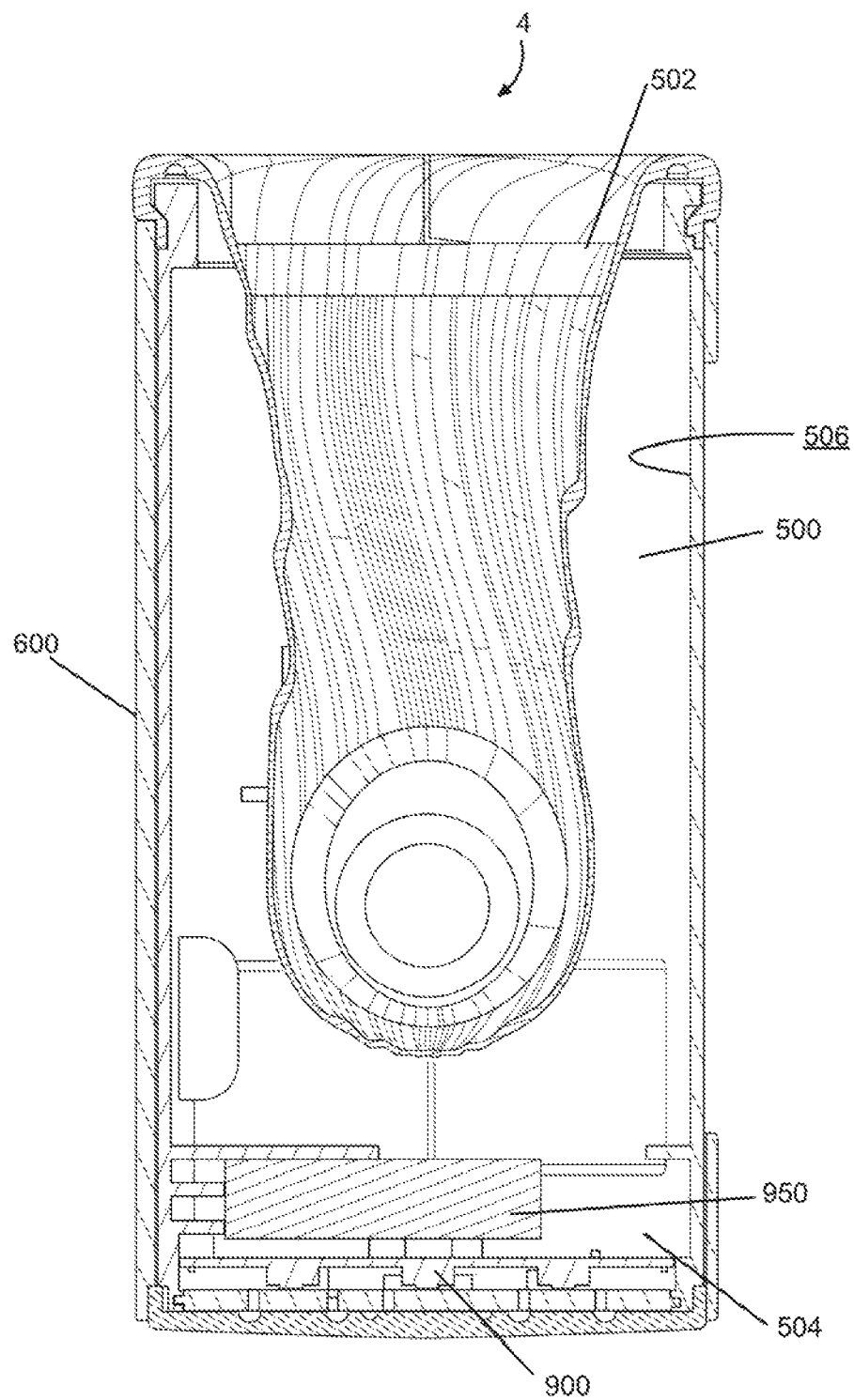
FIG. 21 is a cross-sectional view of the personal massage apparatus illustrated in FIG. 17, taken along line 21-21.
Figure 22:
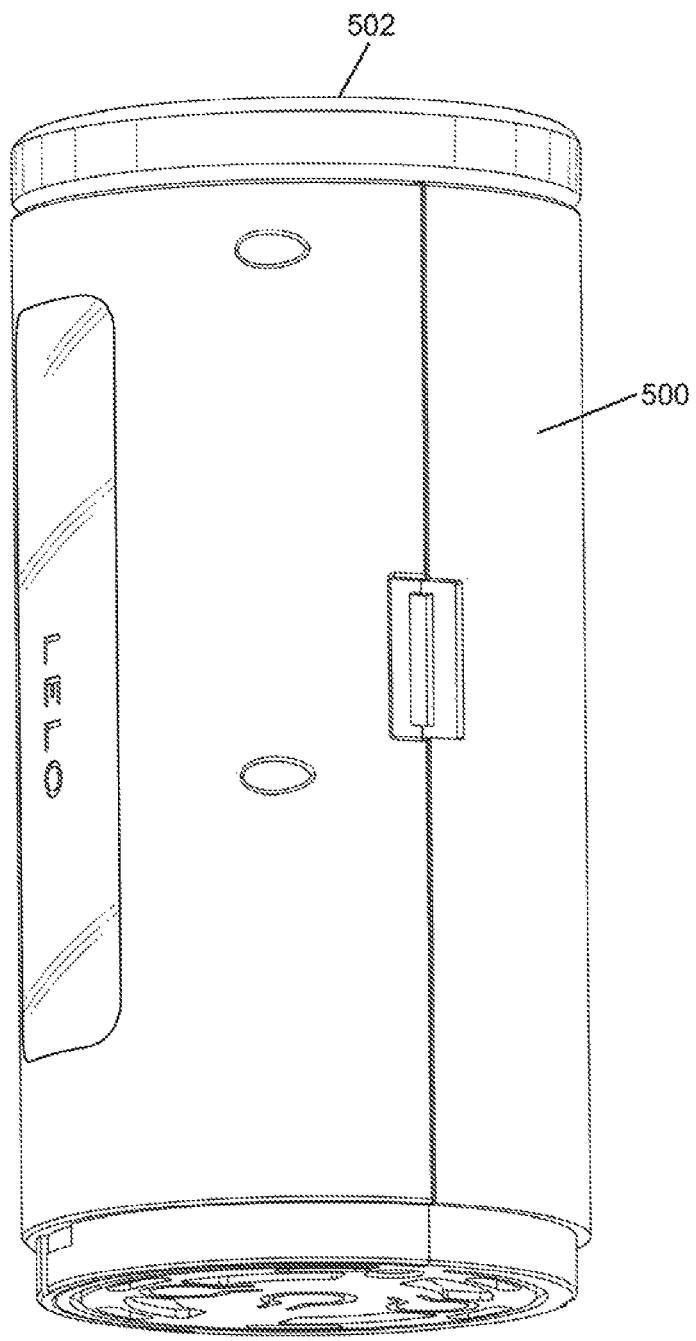
FIG. 22 is a perspective view of the main body of the personal massage apparatus illustrated in FIG. 13 separate from the shell.
Figure 23:
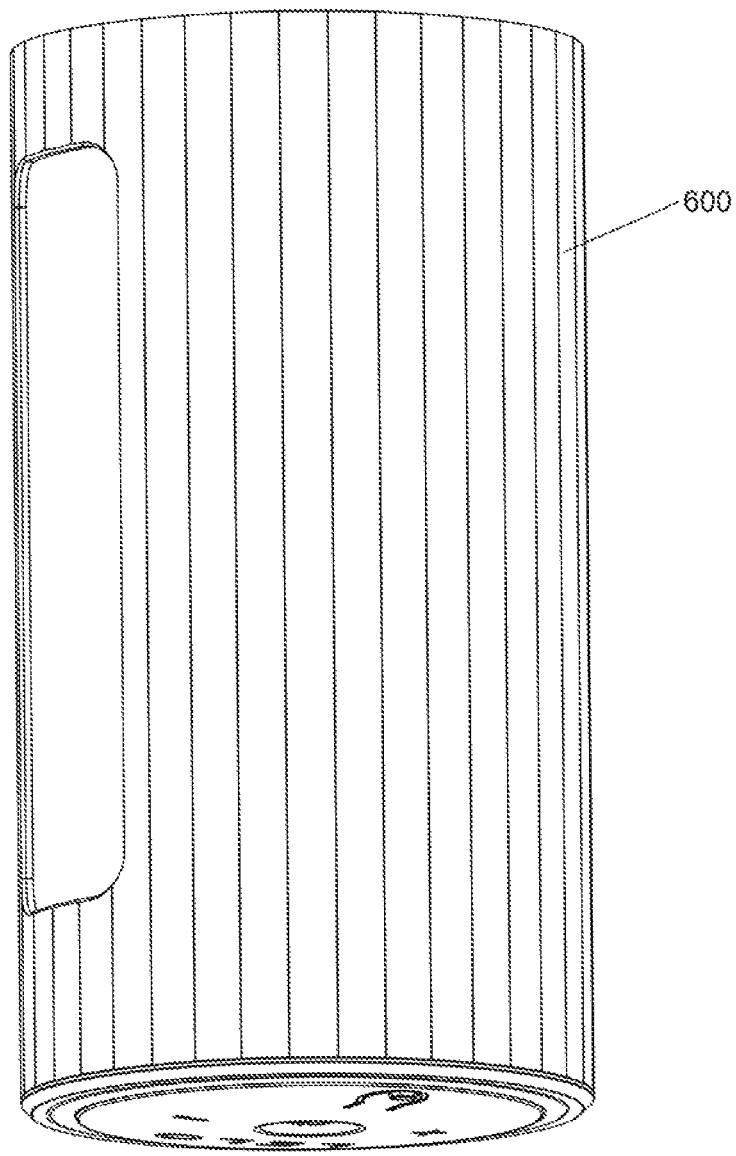
FIG. 23 is a perspective view of the shell of the personal massage apparatus illustrated in FIG. 13 separate from the main body.

As illustrated in FIG. 13, for example, the first end 502 does not include ridges in this embodiment. Instead, the first end 502 is substantially smooth adjacent the shell 600.

Figure 24:
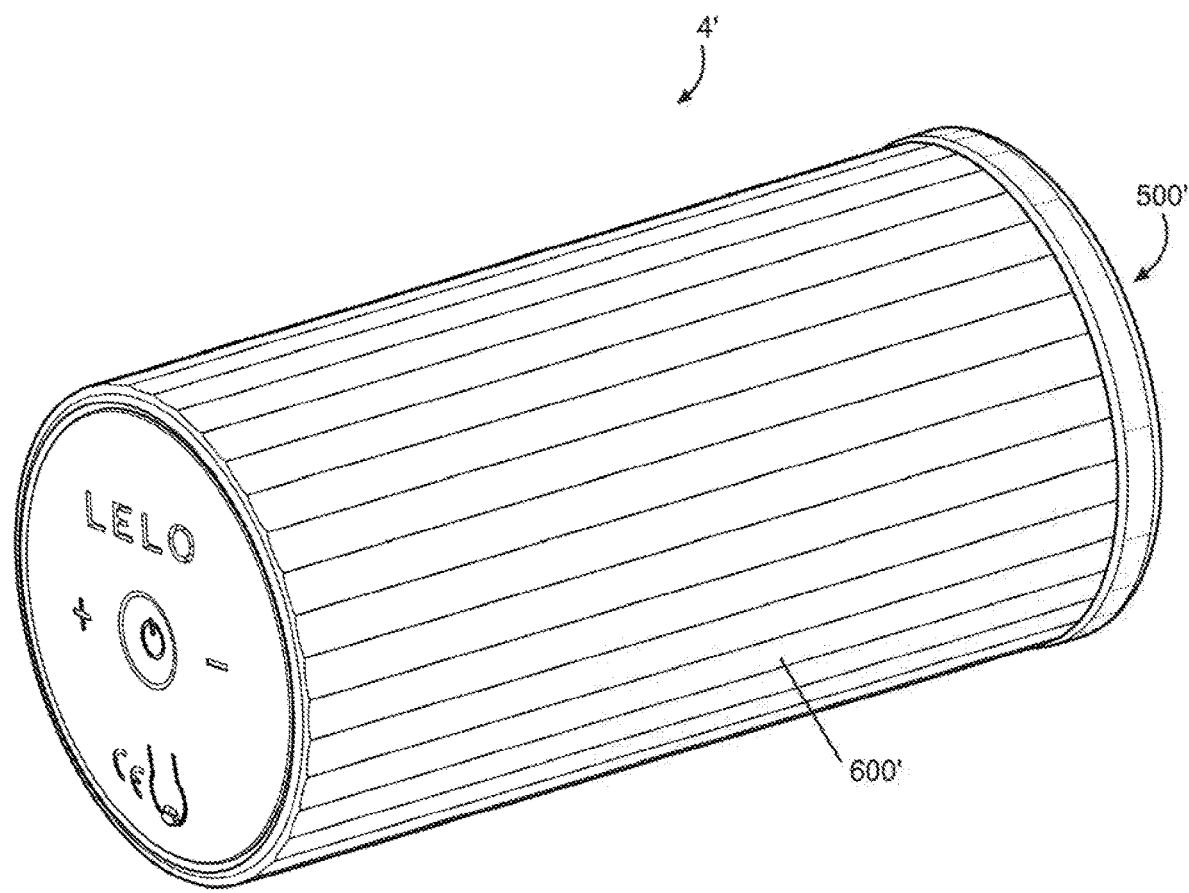
FIG. 24 is a perspective view of an alternative personal massage apparatus.

In an alternative personal massage apparatus 4', illustrated in FIG. 24, the main body 500' and the shell 600' do not cooperatively define a viewing panel. Indeed, the main body 500' does not define a second window and the shell 600' does not define a first window or include a cover. Instead, each of the main body 500' and shell 600' are comprised of their respective materials about their exterior surfaces. A user of the alternative personal massage apparatus 4' is not able to see into the interior of the shell 600' and/or main body 500'. In a different embodiment, personal massage apparatus 2 may not define a viewing panel and/or first or second windows.

Figure 25:
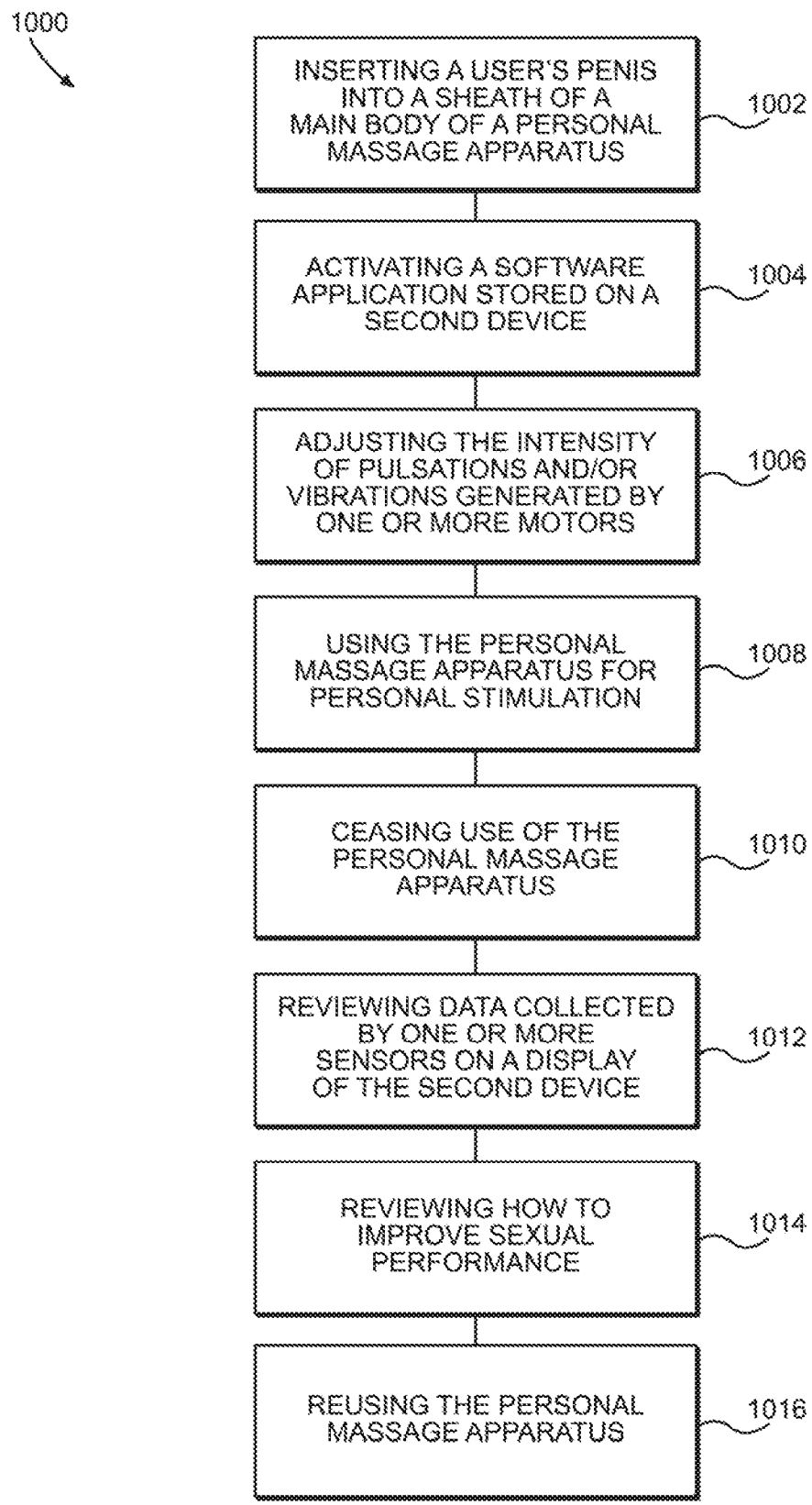
FIG. 25 is a flowchart representation of an example method of using a personal massage apparatus.

FIG. 25 is a flowchart representation of an ex ample method 1000 of using a personal massage apparatus.

An initial step 1002 comprises inserting a user's penis into the sheath of a main body of a personal massage apparatus, such as the sheath 30 of the main body 10 of personal massage apparatus 2. In various other methods, any suitable personal massage apparatus may be selected, including personal massage apparatus 4 or personal massage apparatus 4'.

Another step 1004 comprises activating a software application stored on a second device, such as a mobile phone, that is configured to receive data from the personal massage apparatus 2. This step 1004 is frequently performed before step 1002.

Optionally, another step 1006 comprises adjusting the intensity of the pulsations and/or vibrations generated by one or more motors, such as the first and second motors 200, 250, of the personal massage apparatus 2. The intensity may be increased or decreased.

Another step 1008 comprises the user using the personal massage apparatus 2 to stimulate himself. The user may move and position the personal massage apparatus 2 as described above or in any other manner in order to provide stimulation to himself. Data relating to such use will be collected via first, second, and third sensors, such as first sensor 300, second sensor 330, and third sensor (described above), of the personal massage apparatus 2 during this step.

Another step 1010 comprises ceasing use of the personal massage apparatus 2. Most commonly, this will occur after the user has ejaculated and/or climaxed.

Another step 1012 comprises the user reviewing data collected by one or mare sensors, such as the data collected by one or more of first 300, second 330, and/or third sensors on a display of the second device.

Another step 1014 comprises the user-reviewing suggestions, tips, and/or advice (such as the suggestion, tips, and advice as described above) regarding his sexual performance on the display of the second device.

Optionally, another step 1016 comprises using the personal massage apparatus 2 again and incorporating the suggestions, tips, and advice described in step 514.

It is noted that the method 1000 may be completed in the order illustrated and described. However, the steps may also be completed in any order.

In all examples, a personal massage apparatus may be formed of any suitable material, including presently known and later-developed materials for use in personal massage apparatuses. A skilled artisan will fee able to select an appropriate material or materials for a personal massage apparatus based on various considerations, including, but not limited to, the desired size and shape of the apparatus and its components and the type of stimulation to be produced. Examples of suitable materials that may comprise one or more components include, but are not limited to, silicone, metal, and/or plastic.

Those with ordinary skill in the art will appreciate that various modifications and alternative for the described and illustrated embodiments can be developed in light source of the overall teachings of the disclosure. Accordingly, the particular arrangements disclosed are intended to be illustrative only and not limiting as to the scope of the invention, which is to be given the full breadth of the appended claims and all equivalents thereof.

What is claimed is:

1. A personal massage apparatus configured to stimulate a penis of a user, comprising; an elongate, tubular main body having an open first end, a dosed second end, a middle portion extending from the first end to the second end, and an elongate, flexible sheath disposed within the main body having a proximal end and a distal end, the sheath defining a chamber extending from an opening defined by the proximal end of the sheath to the distal end of the sheath, the sheath being attached to the first end of the main body and comprised of silicone, the sheath configured to receive said penis of said user within the chamber; an elongate, tubular shell attached to and surrounding substantially all of the middle portion of the main body, the shell being comprised of metal; a first motor disposed within the main body and adjacent to the sheath, the first motor configured to drive a rod and a cam and being configured to produce vibrations in order to stimulate said penis, the first motor which is encased in a first housing, said first housing contacting an exterior of the distal end of the sheath via the rod and the cam connected to the first motor and being configured to provide stimulation to a head of said penis; a second motor disposed closer to the proximal end of the sheath than is the first motor, the second motor comprising an oscillating motor, the second motor which is encased in a second housing, said second housing directly contacting an exterior closer to the proximal end of the sheath and being configured to provide stimulation to a shaft of said penis; a controller disposed within the main body and configured to operate the first motor and the second motor; and a first sensor disposed within the main body and adjacent an exterior surface of the sheath, the first sensor configured to sense the proximity of said user to the first sensor.

2. The personal massage apparatus of claim 1, wherein the first sensor comprises a capacitive sensor.

3. The personal massage apparatus of claim 2, wherein the motor will not operate unless the first sensor detects the presence of said user adjacent to the main body.

4. The personal Massage apparatus of claim 3, wherein the first sensor collects data related to said user's performance while using the personal massage apparatus.

5. The personal massage apparatus of claim 4, wherein the data comprises frequency and duration of use and measurements relating to the length of said penis.

6. The personal massage apparatus of claim 1, further comprising a second sensor disposed within the main body and adjacent to the motor, the second sensor configured to detect output produced by the motor.

7. The personal massage apparatus of claim 1, wherein the shell defines a window configured to allow said user to see the main body through the window.

8. The personal massage apparatus of claim 7, further comprising a covering configured to be placed within the window, the covering comprised of plastic.

9. The personal massage apparatus of claim 1, further comprising a user control configured to provide instruction to the controller.

10. The personal massage apparatus of claim 1, wherein an interior surface or the sheath defines grooves extending along an inner surface of the sheath.

11. A personal massage apparatus configured to stimulate a penis of a user, comprising; an elongate, tubular main body having an open first end, a dosed second end, a middle portion extending from the first end to the second end, and an elongate, flexible sheath disposed within the main body having a proximal end and a distal end, the sheath defining a chamber extending from an opening defined by the proximal end of the sheath to the distal end of the sheath, the sheath being attached to the first end of the main body and comprised of silicone, the sheath configured to receive said penis of said user within the chamber; an elongate, tubular shell attached to and surrounding substantially all of the middle portion of the main body, the shell being comprised of metal; a first motor disposed within the main body and adjacent to the sheath, the first motor configured to drive a rod and a cam and being configured to produce vibrations in order to stimulate said penis, the first motor which is encased in a first housing, said first housing contacting an exterior of the distal end of the sheath via the rod and the cam connected to the first motor and being configured to provide stimulation to a head of said penis; a second motor disposed closer to the proximal end of the sheath than is the first motor, the second motor comprising an oscillating motor, the second motor which is encased in a second housing, said second housing directly contacting an exterior closer to the proximal end of the sheath and being configured to provide stimulation to a shaft of said penis; a controller disposed within the main body and configured to operate the first motor and the second motor; a first support column and a second support column disposed within the main body, the first support column and the second support column each contacting an exterior of the sheath and the shell; a first sensor disposed within the main body and adjacent an exterior surface of the sheath; the first sensor configured to sense the proximity of said user to the first sensor; and a second sensor disposed within the main body and adjacent to the first motor, the second sensor configured to detect output produced by the first motor.

12. The personal massage apparatus of claim 11, wherein the first sensor collects data related to said user's performance while using the personal massage apparatus.

13. The personal massage apparatus of claim 12, wherein the data comprises frequency and duration of use and measurements relating to the length of said penis; and wherein the controller transmits the data to a mobile phone having a software application configured to receive and analyze the data.

14. The personal massage apparatus of claim 13, wherein the mobile phone displays the data to said user on a mobile phone display.

15. The personal massage apparatus of claim 14, wherein the mobile phone generates suggestions on how said user may improve sexual performance based on the data.

16. The personal massage apparatus of claim 15, wherein the suggestions include tips on how said user may increase the duration of a sexual encounter.

* * * * *